US007332478B2

(12) United States Patent
Kieny et al.

(10) Patent No.: US 7,332,478 B2
(45) Date of Patent: *Feb. 19, 2008

(54) ANTITUMORAL COMPOSITION BASED ON IMMUNOGENIC POLYPEPTIDE WITH MODIFIED CELL LOCATION

(75) Inventors: Marie-Paule Kieny, Strasbourg (FR); Jean-Marc Balloul, Lingolsheim (FR); Nadine Bizouarne, Schiltigheim (FR)

(73) Assignee: Transgene, Strasbourg (FR)

( * ) Notice: Subject to any disclaimer, the term of this patent is extended or adjusted under 35 U.S.C. 154(b) by 101 days.

This patent is subject to a terminal disclaimer.

(21) Appl. No.: 11/072,288

(22) Filed: Mar. 7, 2005

(65) Prior Publication Data
US 2005/0159386 A1 Jul. 21, 2005

Related U.S. Application Data

(63) Continuation of application No. 09/462,993, filed as application No. PCT/FR98/01576 on Jul. 17, 1998, now Pat. No. 6,884,786.

(30) Foreign Application Priority Data
Jul. 18, 1997 (FR) .................................. 97 09152

(51) Int. Cl.
 *A61K 48/00* (2006.01)
(52) U.S. Cl. ..................................... 514/44; 435/320.1
(58) Field of Classification Search ...................... None
 See application file for complete search history.

(56) References Cited

U.S. PATENT DOCUMENTS

| | | | |
|---|---|---|---|
| 5,185,146 A | 2/1993 | Altenburger | |
| 5,958,736 A * | 9/1999 | St.ang.hl et al. | ............ 435/69.7 |
| 6,096,869 A | 8/2000 | Stanley et al. | |
| 6,316,000 B1 * | 11/2001 | Williamson et al. | ..... 424/191.1 |
| 6,884,786 B1 * | 4/2005 | Kieny et al. | ................... 514/44 |
| 7,101,704 B1 * | 9/2006 | Mosca | ........................ 435/325 |

FOREIGN PATENT DOCUMENTS

| | | |
|---|---|---|
| EP | 83 286 | 7/1983 |
| EP | 206 920 | 12/1986 |
| EP | 0 305 229 | 3/1989 |
| FR | 2 583 770 | 12/1986 |
| FR | 2583429 | 12/1986 |
| FR | 2 722 208 | 1/1996 |
| WO | 87 06260 | 10/1987 |
| WO | 87 07642 | 12/1987 |
| WO | 90/10459 | 9/1990 |
| WO | 90 10459 | 9/1990 |
| WO | 93 00436 | 1/1993 |
| WO | 93/02184 | 2/1993 |
| WO | 94 21680 | 9/1994 |
| WO | 94/28152 | 12/1994 |
| WO | 96/17070 | 6/1996 |
| WO | 96 39178 | 12/1996 |
| WO | 97/04119 | 2/1997 |
| WO | 97 27216 | 7/1997 |

OTHER PUBLICATIONS

Lin et al, Cancer Res Jan. 1, 1996;56:21-6.*
Hagensee et al, Virol 1995;206:174-82.*
Gabuzda et al, J Acquir Immune Defic Syndr 1991;4:34-40.*
Langford et al., "Anchoring a Secreted Plasmodium Antigen on the Surface of Recombinant Vaccinia Virus-Infected Cells Increases Its Immunogenicity", Molecular and Cellular Biology, Sep. 1986, vol. 6, No. 9, pp. 3191-3199, American Society for Microbiology, Washington, DC.
Schlegel et al., "The E5 transforming gene of bovine papillomavirus encodes a small, hydrophobic polypeptide", Science, 1986, vol. 233, No. 4762, pp. 464-467.
Kanda et al., "Human papillomavirus type 16 open reading frame E7 encodes a transforming gene for rat 3Y1 cells", J. Virol, 1988, vol. 62, No. 2, pp. 610-613.
Vousden et al., "The E7 open reading frame of human papillomavirus type 16 encodes a transforming gene", Oncogene Res., 1988, vol. 3, No. 2, pp. 167-175.
Bedell et al., "The E6-E7 region of human papillomavirus type 18 is sufficient for transformation of NIH 3T3 and rat-1 cells", J. Virol., 1987, vol. 61, No. 11, pp. 3635-3640.
Munger et al., "Complex formation of human papillomavirus E7 proteins with the retinoblastoma tumor suppressor gene product", EMBO J., 1989, vol. 8, No. 13, pp. 4099-4105.
Heck et al., "Efficiency of binding the retinoblastoma protein correlates with the transforming capacity of the E7 oncoproteins of the human papillomaviruses", Proc. Natl. Acad. Sci. USA, 1992, vol. 89, No. 10, pp. 4442-4446.
Crook et al., "Degradation of p53 can be targeted by HPV E6 sequences distinct from those required for p53 binding and transactivation", Cell, 1991, vol. 67, No. 3, pp. 547-556.
Miki et al., "A strong candidate for the breast and ovarian cancer susceptibility gene BRCA1", Science, 1994, vol. 226, No. 5182, pp. 66-71.
Wooster et al., "Identification of the breast cancer susceptibility gene BRCA2", Nature, 1995, vol. 378, No. 6559, pp. 789-792.

(Continued)

*Primary Examiner*—Q. Janice Li
(74) *Attorney, Agent, or Firm*—Buchanan, Ingersoll & Rooney, PC

(57) ABSTRACT

Antitumoral compositions can comprise as therapeutic agent one or several immunogenic polypeptides, of which at least one is modified so as to have a cell location different from its native location. Compositions can be based on a recombinant vector expressing such an immunogenic polypeptide. A recombinant vector comprising at least the sequences coding for an immunogenic polypeptide originating from a precocious and/or tardive region of a papillomavirus having a modified location and a viral particle comprising said vector is also described. Finally, therapeutic uses of such a composition, such a recombinant vector and such a viral particle are described.

18 Claims, 5 Drawing Sheets

OTHER PUBLICATIONS

Hareuveni et al., "Vaccination against tumor cells expressing breast cancer epithelial tumor antigen", Proc. Natl. Acad. Scie. USA, 1990, vol. 87, No. 23, pp. 9498-9502.

Branden et al., "Introduction to Protein Structure", 1991, p. 202-214, Garland, NY.

Zhou et al., "Identification of the nuclear localization signal of human papillomavirus type 16 L1 protein", Virology, 1991, vol. 185, No. 2, pp. 625-632.

Tobery et al., "Targeting of HIV-1 antigens for rapid intracellular degradation enhances cytotoxic T lymphocyte (CTL) recognition and the induction of de novo CTL responses in vivo after immunization", J. Exp. Med, 1997, vol. 185, No. 5, pp. 909-920.

Kaisho et al., "The roles of gamma 1 heavy chain membrane expression and cytoplasmic tail in IgG1 responses", Science, 1997, vol. 276, No. 5311, pp. 412-415.

Machamer et al., "A specific transmembrane domain of a coronavirus E1 glycoprotein is required for its retention in the Golgi region", J. Cell Biol., 1987, vol. 105, No. 3, pp. 1205-1214.

Machamer, "Targeting and retention of Golgi membrane proteins", Curr. Opin. Cell Biol., 1993, vol. 5, No. 4, pp. 606-612.

Ensinger et al., "Selection and preliminary characterization of temperature-sensitive mutants of type 5 adenovirus", J. Virol., 1972, vol. 10, No. 3, pp. 328-339.

Ketner et al., "Complementation of adenovirus E4 mutants by transient expression of E4 cDNA and deletion plasmids", Nucleic Acids Res., 1989, vol. 17, No. 8, pp. 3037-3048.

Gooding et al., "Molecular mechanisms by which adenoviruses counteract antiviral immune defenses", Critical Review of Immonology, 1990, vol. 10, No. 1, pp. 53-71.

Freeman et al., "B7, a new member of the Ig superfamily with unique expression on activated and neoplastic B cells", J. of Immunology, 1989, vol. 143, No. 8, pp. 2714-2722.

Taniguchi et al., "Structure and expression of a cloned cDNA for human interleukin-2", Nature, 1983, vol. 302, No. 5906, pp. 305-310.

Phelps et al., "Structure-function analysis of the human papillomavirus type 16 E7 oncoprotein", J. Virol., 1992, vol. 66, No. 4, pp. 2418-2427.

Graham et al., "gene Transfer and Expression Protocols", Methods in Molecular Biology, 1991, vol. 7, pp. 109-128.

Naviaux et al., "Retroviral vectors for persistent expression in vivo", Current Opinion in Biotechnology, 1992, vol. 3, No. 5, pp. 540-547.

Meyer et al., "Mapping of deletions in the genome of the highly attenuated vaccinia virus MVA and their influence on virulence", J. Gen. Virol., 1991, vol. 72, No. pt 5, pp. 1031-1038.

Sutter et al., "A recombinant vector derived from the host range-restricted and highly attenuated MVA strain of vaccinia virus stimulates protective immunity in mice to influenza virus", Vaccine, 1994, vol. 12, No. 11, pp. 1032-1040.

Chen et al., "Breast cancer selective gene expression and therapy mediated by recombinant adenoviruses containing the DF3/MUC1 promoter", J. Clin. Invest., 1995, vol. 96, No. 6, pp. 2775-2782.

Vile et al., "Use of tissue-specific expression of the herpes simplex virus thymidine kinase gene to inhibit growth of established murine melanomas following direct intratumoral injection of DNA", Cancer Res., 1993, vol. 53, No. 17, pp. 3860-3864.

Harris et al., "Gene therapy for cancer using tumour-specific prodrug activation", Gene Therapy, 1994, vol. 1, No. 3, pp. 170-175.

Chakrabarti et al., "Compact, synthetic, vaccinia virus early/late promoter for protein expression", Biotechniques, 1997, vol. 23, No. 6, pp. 1094-1097.

Hammond et al., "A synthetic vaccinia virus promoter with enhanced early and late activity", J. Virological Methods, 1997, vol. 66, No. 1, pp. 135-138.

Kumar et al., "A poxvirus bidirectional promoter element with early/late and late functions", Virology, 1990, vol. 179, No. 1, pp. 151-158.

Felgner et al., "Cationic liposome mediated transfection", Proc. West. Pharmacol. Soc., 1989, vol. 32, pp. 115-121.

Hodgson et al., "Virosomes: cationic liposomes enhance retroviral transduction", Nature Biotechnology, 1996, vol. 14, No. 3, pp. 339-342.

Remy et al., Proc. West. Pharmacol. Soc. 32, 1989, pp. 115-121.

Lynch et al., "Flt3 ligand induces tumor regression and antitumor immune responses in vivo", Nature Medicine, 1997, vol. 3, No. 6, pp. 625-631.

Brasel et al., "Hematologic effects of flt3 ligand in vivo in mice", Blood, 1996, vol. 88, No. 6, pp. 2004-2012.

Marikovsky et al., "Dramatic increase in the numbers of functionally mature dendritic cells in Flt3 ligand-treated mice: multiple dendritic cell subpopulations identified", J. Exp. Med., 1996, vol. 184, No. 5, pp. 1953-1962.

Graham et al., "Characteristics of a human cell line transformed by DNA from human adenovirus type 5", J. Gen. Virol., 1977, vol. 36, No. 1, pp. 59-74.

Imler et al., "Novel complementation cell lines derived from human lung carcinoma A549 cells support the growth of E1-deleted adenovirus vectors", Gene Therapy, 1996, vol. 3, No. 1, pp. 75-84.

Yeh et al., "Efficient dual transcomplementation of adenovirus E1 and E4 regions from a 293-derived cell line expressing a minimal E4 functional unit", J. Virol., 1996, vol. 70, No. 1, pp. 559-565.

Krougliak et al., "Development of cell lines capable of complementing E1, E4, and protein IX defective adenovirus type 5 mutants", Human Gene Therapy, 1995, vol. 6, No. 12 pp. 1575-1586.

Wang et al., "A packaging cell line for propagation of recombinant adenovirus vectors containing two lethal gene-region deletions", Gene Therapy, 1995, vol. 2, No. 10, pp. 775-783.

Mayr et al., Infection 3, 1975, pp. 6-14.

Sutter et al., "Nonreplicating vaccinia vector efficiently expresses recombinant genes", Proc. Natl. Acad. Sci. USA, 1992, vol. 89, No. 22, pp. 10847-10851.

Katz et al., "Immunogenicity of recombinant vaccinia viruses that display the HIV type 1 envelope glycoprotein on the surface of infectious virions", AIDS Res. Hum. Retrov., 1997, vol. 13, No. 17, pp. 1497-1500.

Hanahan, "Studies on transformation of *Escherichia coli* with plasmids", J. Mol. Biol., 1983, vol. 166, No. 4, pp. 557-580.

Bubeck et al., "Rapid cloning by homologous recombination in vivo", Nucleic Acid Res., 1993, vol. 21, No. 15, pp. 3601-3602.

Mackett et al., "Vaccinia virus: a selectable eukaryotic cloning and expression vector Proc", Natl. Acad. Sci. USA, 1982, vol. 79, No. 23, pp. 7415-7419.

Mackett et al., "General method for production and selection of infectious vaccinia virus recombinants expressing foreign genes", J. Virol., 1984, vol. 49, No. 3, pp. 857-864.

Zhou et al., "Expression of vaccinia recombinant HPV 16 L1 and L2 ORF proteins in epithelial cells is sufficient for assembly of HPV virion-like particles", Virology, 1991, vol. 185, No. 1, pp. 251-257.

Altenburger et al., "Partial deletion of the human host range gene in the attenuated vaccinia virus MVA", Arch. Virol., 1989, vol. 105, No. 1-2, pp. 15-27.

Kieny et al., "New versatile cloning and sequencing vectors based on bacteriophage M13", Gene, 1983, vol. 26, No. 1, pp. 91-99.

Davidson et al., "Structure of vaccinia virus early promoters", J. Mol. Biol., 1989, vol. 210, No. 4, pp. 749-769.

Davidson et al., "Structure of vaccinia virus late promoters", J. Mol. Biol., 1989, vol. 210, No. 4, pp. 771-784.

Falkner et al., "*Escherichia coli* gpt gene provides dominant selection for vaccinia virus open reading frame expression vectors", J. Virol., 1988, vol. 62, No. 6 pp. 1849-1854.

Lathe et al., "Plasmid and bacteriophage vectors for excision of intact inserts", Gene, 1987, vol. 57, No. 2-3, pp. 193-201.

Boursnell et al., "Construction and characterization of a recombinant vaccinia virus expressing human papillomavirus proteins for immunotherapy of cervical cancer", Vaccine, vol. 14, No. 16, 1996, pp. 1485-1494, XP002061738.

Meneguzzi et al., "Vaccination Against Papillomavirus-Induced Tumors Using Vacinia Recombinants Expressing Non-Structural Proteins", Journal of Cellular Biochemistry, No. SUP 13, Part C, Jan. 1, 1989, p. 210, XP000121130.

Jarrett et al., "Studies on Vaccination Against Papillomaviruses: Prophylactic and Therapeutic Vaccination With Recombinant Structural Proteins", Nucleic Acids Research, vol. 184, 1991, p. 33042, XP002023588.

Seedorf et al., "Human Papillonmavirus Type 16 DNA Sequence", Virology, vol. 145, No. 1, Aug. 1985, pp. 181-185, XP002059799.

Andrew et al., "The immunogenicity of VP7, a rotavirus antigen resident in the endoplasmic reticulum, is enhanced by cell surface expression", J. Virol. 1990, vol. 64, No. 10, pp. 4776-4783.

Borysiewicz et al., "A recombinant vaccinia virus encoding human papillomavirus types 16 and 18, E6 and E7 proteins as immunotherapy for cervical cancer", Lancet, 1996, vol. 347, No. 9014, pp. 1523-1527.

Genome database for HPV E6, NCBI. 2004.

Britannica Enclopaedia Online, "Chemical Compound Peptides and Proteins", 1994-2000.

Bowie et al., "Deciphering the message in protein sequences: tolerance to amino acid substitutions", Science, 1990, vol. 247, No. 4948, pp. 1306-1310.

Bork, "Powers and pitfalls in sequence analysis", The 70% Hurdle, 2000, vol. 10, No. 4, pp. 398-400.

Scott et al., "The pendred syndrome gene encodes a chloride-iodide transport protein", 1999, vol. 21, pp. 440-443.

Everett et al., "Pendred Syndrome is caused by mutations in a putative sulphate transporter gene (PDS)", Nat Genet, 1997, vol. 17, No. 4, pp. 411-422.

Rudinger, "Characteristics of the amino acids as components of a peptide hormone sequence", 1976; pp. 1-7.

* cited by examiner

ANTITUMORAL COMPOSITION BASED ON IMMUNOGENIC POLYPEPTIDE WITH MODIFIED CELL LOCATION

The subject of the present invention is an antitumoral composition comprising, as therapeutic or prophylactic agent, an immunogenic polypeptide modified so as to have a cell location different from its native location. It also relates to a composition based on a recombinant vector expressing said polypeptide. Such a composition is more particularly intended for the treatment or prevention of lesions associated with papillomaviruses.

It is generally accepted that cancer is a disease which results from a loss of control of cell multiplication. Its causes may be many and may be due in particular to a dysfunction of cellular genes (activation for example by somatic mutation of potentially oncogenic genes; deregulation of expression; inhibition of the expression of tumor suppresser genes) or to the undesirable expression of viral genes.

In humans, papillomaviruses (HPV) are associated with pathologies ranging from benign infection of the skin, to verrucas and to malignant tumors. Among the 75 types of HPV identified up until now, 20 distinct isolates are highly specific to the genital tracts and 5 of them (HPV-16 and 18 and to a lesser degree HPV-31, 33 and 45) are clearly associated with cancer of the cervix and of the lower tracts. A whole series of studies demonstrates the transforming role of these viruses, their specific integration into the genome of neoplastic cells, their gene activity in cancerous cells and the importance of the expression of certain viral genes in maintaining the malignant phenotype of HPV-positive neoplastic cells (Monsenego, J. Impact Medecin, 11 Mar. 1994).

In general, the papillomaviruses are DNA viruses possessing a circular genome of about 7900 base pairs surrounded by a protein capsid. A number of papillomavirus types, in particular bovine papillomaviruses (BPV) and human papillomaviruses (HPV) have been identified (Pfister, 1987, in *The papovaviridae: The Papillomaviruses*, Salzman and Howley edition, Plenum Press, New York, p 1-38). Their genome comprises an early region containing the reading frames E1, E2, E4, E5, E6 and E7 and a late region encoding the capsid proteins L1 and L2.

The early proteins have the capacity to bind DNA and are found predominantly in the nucleus. The products of expression E1 and E2 regulate the viral replication and the expression of the viral genes whereas those of the E5, E6 and E7 regions are involved in the processes of oncogenic transformation of the infected cells. In this regard, it has been shown experimentally that the BPV-1 E5 protein can transform cells in vitro (Schlegel et al., 1986, Science 233, 464-467). The transforming power of E7 has been demonstrated for HPV-16 and HPV-18 (Kanda et al., 1988, J. Virol. 62, 610-613; Vousden et al., 1988, Oncogene Res. 3, 1-9; Bedell et al., 1987, J. Virol. 61, 3635-3640) and correlated with its capacity to bind the product of the retinoblastoma (Rb) gene (Munger et al., 1989, EMBO J. 8, 4099-4105; Heck et al., 1992, Proc. Natl. Acad. Sci. USA 89, 4442-4446). Moreover, Crook et al. (1991, Cell 67, 547-556) have shown that the E6 antigen of HPV-16 and 18 can complex the product of the p53 gene, which explains its predominant role in cell transformation.

The pathologies associated with the HPV viruses pose a therapeutic problem because of their persistent and recurring nature. Although the conventional approaches remain surgery and chemotherapy, immunotherapy is now envisaged for the treatment of these diseases. The ideal candidate vaccine should, for preventive purposes (immunoprophylaxy), prevent the infection from becoming durably established and from spreading to the neighboring tissues and, for curative properties (immunotherapy), reduce the tumor progression in the infected patients. It has been proposed up until now to use the capsid antigens to induce the production of antibodies against the epitopes located at the surface of the viral particles and the early proteins to establish cellular immunity against cells infected after integration of the viral DNA.

In this regard, European patent EP 0,462,187 describes a therapeutic approach involving administration of poxvirus expressing the papillomavirus early genes. The vaccination approach described in WO 93/02184 is based on the use of capsid antigens as immunogenic agents and in particular of viral particles empty of DNA (VLP for virus-like particles) reconstituted in vitro. French application 96 09584 discloses a composition combining the preventive effect provided by the early polypeptides and the curative effect conferred by the papillomavirus late polypeptides. However, up until now, viral proteins have been used which are optionally mutated so as to abolish their transforming activity, but which are nevertheless native from the point of view of their cellular location.

The present invention proposes to use immunogenic proteins whose location has been modified with the aim of enhancing their accessibility to the host's immune system, in order to enhance or stimulate an immune response toward the tumor or the cancer to be treated, whether it is specific or non-specific and of the humoral type (production of antibodies) or of the cellular type (cytotoxic response CTL).

The HPV-16 E6 and E7 nuclear antigens have now been modified by introducing appropriate anchoring and secretory sequences so as to confer a transmembrane presentation on them. The change in location has a beneficial effect on the immune response which results in a higher antitumoral activity in animals treated with a vaccinia virus co-expressing the membrane E6 and E7 antigens and human IL-2, compared with those which received an equivalent virus producing the nuclear antigens. The aim of the present invention is to make available to the public antitumoral compositions which are more effective than the compositions of the prior art, for inhibiting, at least partially, the establishment or the progression of a tumor or of a cancer. A particularly useful application is the treatment of HPV infections and more particularly of serious pathologies such as cancer of the cervix.

Accordingly, the subject of the present invention is an antitumoral composition comprising, as therapeutic or prophylactic agent, one or more immunogenic polypeptides, at least one of said polypeptides being modified so as to have a location different from its native location.

For the purposes of the present invention, the term "immunogenic polypeptide" designates a polypeptide whose equivalent does not exist in the normal cells. A preferred example consists of a tumor-specific antigen. By way of illustration, there may be mentioned the cellular antigens whose expression occurs during the feto-embryonic period and regresses at birth until it disappears, the antigens which are normally expressed at a very low level and which, when expressed at a high level, become characteristic of a tumor, the cellular antigens whose structure or conformation is modified or alternatively the noncellular antigens, in particular the viral antigens which are derived from an oncogenic virus. They may be for example the products of expression of the genes BRCA-1 (Miki et al., 1994, Science 226, 66-71), BRCA-2 (Wooster et al., 1995, Nature 378, 789-792), MUC-1 (Hareuveni et al., 1990, Proc. Natl. Acad.

Sci. USA 87, 9498-9502), CEA and the like, of which certain mutations or the overexpression are involved in the cancerous development. As regards viral antigens, there may be mentioned more particularly the products of expression of the papillomavirus early or late genes, Epstein-Barr virus EBNA-1, the antigens of the HTLV (Human T Lymphocyte Virus) I and II viruses or of the hepatitis B and C viruses. The tumor-specific antigens are widely described in the literature accessible to persons skilled in the art.

The essential characteristic of the polypeptide in use in the present invention is having a location different from its native location. The mechanisms of transport and the signals involved are described in cell biology books (see for example Molecular Biology of the Cell, Third Ed. Garland Publishing Inc. NY & London). Briefly, the great majority of polypeptides are synthesized on free ribosomes in the cytosol where they exert their activity. However, some polypeptides have a different cellular destination which is generally determined by the presence of appropriate peptide signals, and must be transported up to it. Thus, the polypeptides intended to be exported toward the plasma membrane or secreted outside the cell are synthesized by ribosomes associated with the endoplasmic reticulum (ER) generally in the form of precursors comprising, at their amino-terminal end, a secretory sequence (or signal peptide) which initiates their passage into the ER. It is then removed by a specific endopeptidase to give the mature polypeptide. A secretory sequence usually comprises 15 to 35 essentially hydrophobic amino acids. There is no consensus sequence and it appears that it is the secondary structure which determines recognition by the endopeptidase. However, the proteolytic cleavage most often takes place after a glycine, serine or alanin residue.

The membrane proteins generally comprise an anchoring sequence of a highly hydrophobic nature which remains inserted in the plasma membrane. The polypeptide may be transmembranous with one of its ends exposed to the outside of the cell, the anchoring sequence crossing the membrane and the other end on the cytosolic side. In most cases, the polypeptide chain embedded in the lipid double layer of the membrane has an α-helix conformation (see for example Branden and Tooze, 1991, in Introduction to Protein Structure p. 202-214, NY Garland).

As for the nuclear location, it may be conferred by the presence of a short so-called nuclear localization sequence (NLS) composed mainly of positively charged residues such as lysine and arginine. There may be mentioned by way of examples nuclear translocation signals KRKKRK (SEQ ID NO: 24) and RKRRKR (SEQ ID NO: 25) present in the HPV L1 and L2 polypeptides (Zhou et al., 1991, Virology 185, 625-632). However, some polypeptides exerting their function inside the nucleus do not possess a typical NLS sequence. It is the case of the papillomavirus E6 and E7 antigens.

The immunogenic polypeptide contained in the composition according to the invention may result from the introduction and/or deletion of appropriate localization signals within a native polypeptide, a fragment thereof, a chimera comprising sequences of different origins or a variant (deletion, insertion and/or substitution of one or more amino acids). More particularly, its amino acid sequence exhibits a degree of similarity, with all or part of the sequence of the native polypeptide from which it is derived, greater than 70%, advantageously greater than 80% and preferably greater than 90%. The degree of similarity can be easily calculated with the aid of an appropriate computer program or by aligning the sequences so as to obtain the maximum degree of homology and by counting the number of positions in which the amino acids of the two sequences are found to be identical relative to the total number of positions.

Persons skilled in the art know the signals which allow a change in the cellular presentation of a polypeptide. In the case where it is desirable for the immunogenic polypeptide to be secreted, the addition of a secretory sequence to its amino-terminal end will allow its transport via the ER to the outside of the host cell. The insertion preferably takes place immediately downstream of the codon for initiation of translation. In the context of the present invention, it may be advantageous to mutate/delete all or part of the residues determining the native location, in order to avoid interference. For example, if the native polypeptide has a membrane destination, it already comprises a secretory sequence and the hydrophobic anchoring sequence will be optionally mutated or deleted. In addition, the inactivation (by mutation/deletion) of the native signals can allow a cytoplasmic location. The cytoplasmic presentation of an immunogenic peptide normally having a different cell location (for example nuclear, membrane, secreted and the like) can promote peptide presentation mediated by the class I antigens of the major histocompatibility complex and the CTL response in vivo (Tobery and Siliciano, 1997, J. Exp. Med. 5, 909-920). Another embodiment which may be envisaged consists in fusing the immunogenic polypeptide with ubiquitin, also with the aim of stimulating a potent CTL response.

Advantageously, a composition according to the invention comprises an immunogenic polypeptide modified so as to have a membrane location, preferably by inserting a membrane anchoring sequence and, in the case where the native polypeptide lacks it, a secretory sequence. The preferred site of insertion of the secretory sequence is the N-terminal end, as indicated above, and that of the membrane anchoring sequence is the C-terminal end, for example immediately upstream of the stop codon. In this context, it may also be advantageous to carry out the mutation/deletion of all or part of the native localization signals (for example NLS sequence) so as not to interfere with the new location.

The choice of the localization signal which can be used in the context of the present invention is vast. It may be derived from any protein comprising it, of eucaryotic origin or otherwise (virus, parasite, fungus and the like) as long as it is recognized by the cell to be treated. It may be natural or synthetic, heterologous or homologous with respect to the latter. It may also comprise one or more modifications relative to the signal from which it is derived, with the proviso that it/they does not affect its function. As a guide, it will be preferable to use the membrane anchoring and/or secretory sequences of the rabies glycoprotein, of the HIV virus env glycoprotein or of the measles virus F protein. In the case where the modification of the immunogenic polypeptide involves several localization signals (for example membrane anchoring and secretory sequence), these may have a common or different origin.

It is also possible to use localization signals targeting a particular cellular compartment. There may be mentioned in particular a consensus sequence for endocytosis (for example present ni the C-terminal region of the immunoglobin IgG1 heavy chains having the sequence IPNYRNM (SEQ ID NO: 26); Kaisho et al. 1997, Science 276, 412-414) or a sequence allowing targeting into the membrane of the Golgi apparatus (Mochamer and Rose, 1987, J. Cell Biol. 105, 1205-1214; Mochamer, 1993, Curr. Opin. Cell Biol. 5, 606-612). It is possible in particular to envision the use of Coronavirus E1 glycoprotein-derived sequences disclosed in the Swiss-Prot data bank under accession P11222. The incorporation of this type of sequence at the C-terminal end of the immunogenic polypeptide is preferred.

Moreover, the modification of cell location may be performed by any conventional technique, in particular by site-directed mutagenesis, ligation of exogenous signals or PCR.

According to a preferred embodiment, an antitumoral composition according to the invention is intended for the treatment or prevention of papillomavirus infections and of disorders resulting therefrom, in particular low-grade cervical dysplasias and cancer of the cervix. According to this embodiment, it comprises at least one immunogenic polypeptide originating from an early and/or late region of a papillomavirus, in particular of a high-risk virus such as HPV-16, 18, 31, 33 or 45.

In accordance with the aims pursued by the present invention, it is possible to use one or more immunogenic papillomavirus polypeptides of any type. As recalled above, their genome encodes 8 polypeptides, two late polypeptides L1 and L2 comprising the viral capsid and 6 early polypeptides (E1, E2, E4, E5, E6 and E7) involved in the regulation, the maintenance of the viral genome and the transformation of the infected cells.

As regards an immunogenic polypeptide of the early type, the choice is advantageously made to use a polypeptide derived from E6 or E7, modified in particular so as to have a membrane location. Given the observations recalled above on the transforming power, there is preferably used a non-oncogenic variant mutated in the region involved in the process of cell transformation. Such variants are described in the literature (Mungeret al., 1989, EMBO J., 8, 4099-4105; Crook et al., 1991, Cell 67, 547-556; Heck et al., 1992, Proc. Natl. Acad. Sci. USA 89, 4442-4446; Phelps et al., 1992, J. Virol. 66, 2148-2427). An immunogenic polypeptide which is particularly suitable for the purpose of the present invention is the HPV-16 E6 antigen deleted for residues 111-115 (+1, representing the first amino acid of the native viral antigen) and fused with the secretory and anchoring signals of the measles F protein (SEQ ID NO:1). It is also possible to use the HPV-16 E7 antigen deleted for residues 22 to 25 and fused with the anchoring and secretory sequences of the rabies glycoprotein (SEQ ID NO:2).

The antitumoral composition according to the invention may also comprise an immunogenic polypeptide originating from the late region of a papillomavirus, derived from L1 or L2.

Of course, the antitumoral composition according to the invention may comprise several immunogenic polypeptides, of which at least one has a cell location different from its native location. There may be mentioned, to illustrate a composition combining several polypeptides derived from papillomaviruses, those which may have a common or different origin (for example HPV-16 and 18 with the aim of broadening the activity spectrum). A composition combining several polypeptides of early origin would make it possible to enhance the therapeutic effects. The combination of the polypeptides derived from L1 and L2 could have a beneficial effect on the preventive properties of the composition. Finally, a composition which is most particularly suitable for the aims pursued by the present invention comprises at least one early polypeptide and at least one late polypeptide of a papillomavirus so as to combine the preventive and curative effect. According to a preferred embodiment, at least one of the immunogenic polypeptides of early origin is modified so as to have a membrane location by the addition of secretory and anchoring sequences such as those cited above.

In this regard, a preferred composition according to the invention comprises:

(1) an immunogenic polypeptide having a sequence homologous or identical to all or part of that shown in SEQ ID NO: 1, (2) an immunogenic polypeptide having a sequence homologous or identical to all or part of that shown in SEQ ID NO: 2, (3) an immunogenic polypeptide having a sequence homologous or identical to all or part of that shown in SEQ ID NO: 1 and an immunogenic polypeptide having a sequence homologous or identical to all or part of that shown in SEQ ID NO: 2, (4) an immunogenic polypeptide having a sequence homologous or identical to all or part of that shown in SEQ ID NO: 1, an immunogenic polypeptide derived from the protein L1 of a papillomavirus and/or an immunogenic polypeptide derived from the protein L2 of a papillomavirus, (5) an immunogenic polypeptide having a sequence homologous or identical to all or part of that shown in SEQ ID NO: 2, an immunogenic polypeptide derived from the protein L1 of a papillomavirus and/or an immunogenic polypeptide derived from the protein L2 of a papillomavirus, or (6) an immunogenic polypeptide having a sequence homologous or identical to all or part of that shown in SEQ ID NO: 1, an immunogenic polypeptide having a sequence homologous or identical to all or part of that shown in SEQ ID NO: 2, an immunogenic polypeptide derived from the protein L1 of a papillomavirus and/or an immunogenic polypeptide derived from the protein L2 of a papillomavirus.

The term "homologous" refers to a degree of identity with said sequence greater than 70%, advantageously greater than 80%, preferably greater than 90% and most preferably greater than 95%.

Advantageously, an antitumoral composition according to the invention may comprise, in addition, at least one compound enhancing its antitumoral effect, with the aim of increasing the intensity of the immune response specifically or otherwise. In addition to the adjuvants, the immunostimulators represent particularly preferred compounds. "Immunostimulator" is understood to mean a compound having the capacity to strengthen a humoral immune response so as to amplify the production of antibodies directed against the immunogenic polypeptide or a cell-mediated immune response, so as to trigger a significant cytotoxic response against tumor or infected cells. As a guide, the immunostimulation may be evaluated in a cancerous animal model by comparing the rate of rejection in an animal treated with the immunogenic polypeptide, in the presence and in the absence of the immunostimulator. More generally, the means for demonstrating an immunostimulation are indicated in Roitt (*Immunology,* $4^{th}$ edition, Moby Ltd). One of the advantages of such a composition is that it combines the specific immunity induced by the immunogenic polypeptide and the aspecific immunity induced by the immunostimulatory molecule.

In the context of the present invention, it is possible to use a native immunostimulator, in particular of human origin, a portion thereof, a chimera obtained from the fusion of sequences of diverse origins or a mutant, on the condition, however, that the immunostimulatory function is conserved. Among all the molecules which may be envisaged, it is preferable to use an immunostimulator chosen from interleukin-2, interleukin-7, interleukin-12 and the coadhesion molecules B7.1 and B7.2. It should be stated that interleukin-2 and the molecule B7.1 are particularly preferred.

In general, the immunogenic and immunostimulatory polypeptides may be produced by conventional chemical synthesis methods or by recombinant DNA techniques (see for example Maniatis et al., 1989, *Laboratory Manual*, Cold Spring Harbor, Laboratory Press, Cold Spring Harbor, N.Y.). More particularly, a method of preparation comprises the act of culturing a cell transformed with a DNA fragment encoding the polypeptide in question to generate a producing cell and the act of harvesting said polypeptide from the culture. The producing cell may be of any origin and without limitation a bacterium, a yeast or a mammalian cell, insofar as the DNA fragment considered is either integrated into its genome or integrated into an appropriate expression vector. Of course, the DNA fragment is placed under the control of transcriptional and translational signals allowing its expression in the producing cell. Expression vectors and control signals are known to persons skilled in the art.

The present invention also relates to an antitumoral composition comprising, as therapeutic or prophylactic agent, at least one recombinant vector comprising the sequences encoding one or more immunogenic polypeptides, at least one of said polypeptides being modified so as to have a location different from its native location and, optionally, a compound enhancing the antitumoral effect. This type of composition has the advantage of an inexpensive production and of high stability under varying environmental conditions. In particular, the storage conditions are less constraining. The polypeptides have the characteristics as defined above.

The sequences encoding the immunogenic polypeptide or enhancing the antitumoral effect may be obtained by cloning, by PCR (Polymerase Chain Reaction) or by chemical synthesis according to the conventional techniques in common use and using the literature data. As regards the preferred embodiment, the sequences encoding the papillomavirus polypeptides may be chosen from papillomavirus-positive cells obtained from patients or from collections. The insertion of the appropriate localization signals may be carried out by molecular biology techniques. The sequences encoding the immunostimulator may be cloned from the cellular DNA or from the messenger RNAs of a cell in which it is expressed. Persons skilled in the art are capable of generating the appropriate probes or primers from the published data. It should be stated that the nucleotide sequence of the HPV-16 and 18 genomes is disclosed in Genbank under accession numbers K02718 and X05015 respectively. The sequence of the human IL-2 gene is described in French patent 85 09480 and in Taniguchi et al. (1983, Nature 302, 305-311) and that encoding the B7.1 antigen in Freeman et al. (1989, J. of Immunology 143, 2714-2722).

A vector which can be used in the context of the invention may be a plasmid or viral vector, derived in particular from a poxvirus, an adenovirus, a retrovirus, a herpesvirus or an adenovirus-associated virus. Advantageously, it will be a nonintegrative vector having an attenuated virulence. Such vectors and the techniques for their preparation are known to persons skilled in the art.

In the case where an adenoviral vector is used, use will be preferably made of a nonrepetitive factor by deleting regions essential for replication and, in particular, most of the E1 region so as to avoid its propagation in the host organism or the environment. It goes without saying that other regions of the adenoviral genome, in particular within the E2, E4 and/or L1-L5 regions, may be modified or deleted, insofar as the defective essential functions are complemented in trans. To illustrate these embodiments, there may be mentioned the heat-sensitive mutation affecting the DBP (for DNA Binding Protein) gene of the E2A region (Ensinger et al., 1972, J. Virol. 10, 328-339). A partial deletion of the E4 region, with the exception of the sequences encoding the open reading frames (ORF) 6 and 7 may also be envisaged (Ketner et al., 1989, Nucleic Acids Res. 17, 3037-3048). Another possibility is the total deletion of the transcriptional unit E4. Moreover, the adenoviral vector according to the invention may lack all or part of the nonessential region E3. According to this alternative, it may be advantageous to conserve, nevertheless, the E3 sequences encoding the polypeptides which make it possible to escape the host's immune system, in particular the glycoprotein gp19k (Gooding et al., 1990, Critical Review of Immunology 10, 53-71). A preferred adenoviral vector according to the invention will exhibit minimum retention of the sequences essential for encapsidation, namely the 5' and 3' ITRs (Inverted Terminal Repeat) and the encapsidation region. It should be stated that it may be derived from a human or animal adenovirus and from any serotype. The subgroup C human adenoviruses and in particular the adenoviruses 2 (Ad2) and 5 (Ad5) are most particularly suitable for carrying out the invention. The different adenoviral vectors as well as the techniques for their preparation are conventional and are described in Graham and Prevect (1991, in *Methods in Molecular Biology*, vol 7, p 109-128; Ed: E. J. Murey, The Human Press Inc.) and in international application WO 94/28152. For example, it may be generated in vitro in *Escherichia coli* (*E. coli*) by ligation or homologous recombination (see for example international application WO96/17070) or by recombination in a complementation line.

If a retrovirus is used, the LTRs (Long Terminal Repeat) and the encapsidation sequences (see for example Naviaux and Verma, 1992, Current Opinion in Biotechnology 3, 540-547) are conserved. The sequence encoding the immunogenic polypeptide(s) may be placed under the control of the retroviral LTR or of an internal promoter such as those described below. It may be derived from a retrovirus of any origin (murine, primate, feline, human and the like) and in particular from MoMuLV (Moloney murine leukemia virus), MVS (Murine sarcoma virus) or Friend murine retrovirus (Fb29). It may also comprise modifications especially at the level of the LTRs (replacement of the promoter region by a eucaryotic promoter) or of the encapsidation region (replacement by a heterologous encapsidation region, for example of the VL30 type) (see French applications 94 08300 and 97 05203).

According to an advantageous embodiment, a recombinant vector according to the invention is derived from a poxvirus and in particular from an avian poxvirus, such as a canary poxvirus, from a fowlpox or from a vaccinia virus, the latter being preferred. Among all the vaccinia viruses which may be envisaged in the context of the present invention, the Copenhagen, Wyeth and modified Ankara (MVA for Modified Vaccinia Virus Ankara) strains are preferably chosen.

Generally, the site of insertion is chosen in a region nonessential to replication, such that the replication and propagation capacities of the recombinant virus are not impaired. As a guide, when a Copenhagen strain of virus is used, the preferred site of insertion is the TK locus, which has the effect of inactivating the latter and thereby facilitating the selection of the recombinants. It is also possible to use the K1L locus. As regards an MVA virus, the insertion of the recombinant (immunogenic and immunostimulatory) sequences may be carried out inside at least one of the excisions I to VI and, in particular II or III (Meyer et al., 1991, J. Gen. Virol. 72, 1031-1038; Sutter et al., 1994, Vaccine 12, 1032-1040). The insertion may also take place in an essential viral region, such as the D4R region, it being possible for the defective function to be provided in trans for example by means of a complementation line.

Of course, in the context of the present invention, the sequences encoding the immunogenic polypeptide or enhancing the antitumoral effect are placed under the control of elements necessary for their expression in a host cell or organism. They include the elements for regulating transcription as well as signals for initiation and termination of translation. Among them, the promoter is of particular importance. In general, use will be made of a promoter which is functional in the host organism or cell which it is desired to treat and which is suitable for the vector used. In addition, it may be modified so as to contain regulatory sequences, for example an element activating transcription or sequences responding to certain cellular signals. In this regard, it may be advantageous to use a tissue-specific promoter since the lesions associated with papillomaviruses are located at the level of the genital tracts or a promoter responding to signals which are specifically tumoral (for example which is activated in the presence of growth factors which are generally overexpressed by tumor cells) so as to limit expression to the tumor cells alone.

Among the promoters which may be envisaged in the context of the invention, there may be mentioned the SV40 (Simian Virus 40) promoter, the HMG (Hydroxy-Methyl-Glutaryl-coenzyme A) promoter, the TK (Thymidine Kinase) promoter, the CMV (cytomegalovirus) promoter, the RSV (Rous Sarcoma Virus) promoter, the MLP promoter (Major Late Promoter) which is suitable for adenoviral vectors and the LTR of the Mo-MLV (Moloney Murine Leukemia Virus) which is more specific for the retroviral vectors. The cytomegalovirus (CMV) early promoter is most particularly preferred. It may also be a promoter stimulating expression in a tumor or cancer cell. There may be mentioned in particular the promoters of the MUC-1 gene which is overexpressed in breast and prostate cancers (Chen et al., 1995, J. Clin. Invest. 96, 2775-2782), the tyrosinose gene which is overexpressed in melanomas (Vile et al., 1993, Cancer Res. 53, 3860-3864) and the ERB-2 gene which is overexpressed in cancers of the breast and of the pancreas (Harris et al., 1994, Gene Therapy 1, 170-175). The promoters in question are described in the literature and may be cloned from the cellular or viral genome by conventional techniques.

As regards a poxviral vector, use may be made of a pox promoter, for example 7.5K, H5R, TK, p. 28, p. 11 or K1L of the vaccinia virus. A synthetic promoter is also suitable for carrying out the present invention (see for example Chakrabarti et al., 1997, Biotechniques 23, 1094-1097; Hammond et al., 1997, J. Virological Methods 66, 135-138 and Kumar and Boyle, 1990, Virology 179, 151-158). In this regard, it is advantageously a chimeric promoter between a late promoter and an early promoter.

Moreover, the elements necessary for the expression may also comprise sequences enhancing expression or maintenance in the host cell (intron, sequence for terminating transcription, site of initiation of translation and the like). However, in the case of a poxviral vector, the use of introns will be avoided.

A composition according to the invention may comprise one or more recombinant vectors expressing sequences corresponding to the chosen polypeptides placed under the control of independent or common elements. According to the latter option, use may be made of sequences allowing initiation of translation internally (IRES) or of fusions in phase of the different genes.

The general conditions for producing a recombinant vector used in the present invention are widely described in the state of the art. As regards a poxviral vector, reference may be made to European patent EP 83 286 whose content is incorporated therein by reference. These conditions are applicable to the other viruses acceptable as vector which possess a genomic region into which the units of expression may be incorporated. Of course, they may be inserted into the same locus or a different locus.

In accordance with the aims pursued by the present invention, a recombinant vector may in addition comprise a unit for expressing a selectable marker gene so as to facilitate the steps of isolation and purification of the recombinant virus. There may be mentioned in particular the neo gene which confers resistance to the antibiotic G418, the pac gene for resistance to puromycin, the TK gene of the herpes simplex virus type 1 (HSV-1) which confers sensitivity to certain nucleoside analogs such as ganciclovir or acyclovir, the gpt (xanthine guanine phosphoribosyl transferase) gene, the bacterial genes LacZ encoding β-galactosidase and gus A encoding β-glucuronidase. The latter two enzymatic markers make it possible to identify the recombinant viruses by staining in the presence of the substrates X-Gal (5-bromo-4-chloro-3indolyl-β-D-galactopyranoside) and XglcA (5-bromo-6-chloro-3-indolyl-β-D-glucoronide) respectively.

A preferred antitumoral composition is intended for the treatment or the prevention of a papillomavirus infection or tumor, and comprises at least one vaccinia virus of the Copenhagen or MVA strain into which there have been inserted:

(1) the sequences encoding an immunogenic polypeptide having a sequence homologous or identical to all or part of that shown in SEQ ID NO: 1, (2) the sequences encoding an immunogenic polypeptide having a sequence homologous or identical to all or part of that shown in SEQ ID NO: 2, (3) the sequences encoding an immunogenic polypeptide having a sequence homologous or identical to all or part of that shown in SEQ ID NO: 1 and an immunogenic polypeptide having a sequence homologous or identical to all or part of that shown in SEQ ID NO: 2, (4) the sequences encoding an immunogenic polypeptide having a sequence homologous or identical to all or part of that shown in SEQ ID NO: 1, an immunogenic polypeptide derived from the protein L1 of a papillomavirus and/or an immunogenic polypeptide derived from the protein L2 of a papillomavirus, (5) the sequences encoding an immunogenic polypeptide having a sequence homologous or identical to all or part of that shown in SEQ ID NO: 2, an immunogenic polypeptide derived from the protein L1 of a papillomavirus and/or an immunogenic polypeptide derived from the protein L2 of a papillomavirus, or (6) the sequences encoding an immunogenic polypeptide having a sequence homologous or identical to all or part of that shown in SEQ ID NO: 1, an immunogenic polypeptide having a sequence homologous or identical to all or part of that shown in SEQ ID NO: 2, an immunogenic polypeptide derived from the protein L1 of a papillomavirus and/or an immunogenic polypeptide derived from the protein L2 of a papillomavirus.

Said composition may also comprise the sequences encoding an immunostimulator preferably chosen from IL-2 or B7.1. It may be carried by one of the recombinant vectors allowing the expression of the immunogenic gene(s) or by an independent vector.

A composition according to the invention may be prepared according to methods known in the field of vaccines and the applicable doses may vary within a broad range. They depend in particular on the polypeptides and the vector used, the pathology to be treated, the condition of the patient and on other parameters which may be evaluated by the clinician. However, in general, the virus dose will be $10^4$ to $10^{13}$, advantageously $10^5$ to $10^{12}$ and preferably $10^5$ to $10^9$ plaque-forming units (pfu) when the therapeutic agent is a viral vector and 0.05 to 500 mg, advantageously 0.5 to 200 mg and preferably 1 to 100 mg when the therapeutic agent is of polypeptide origin.

A composition according to the invention may be administered by any conventional route of administration, preferably by the systemic route and in particular by the intramuscular, intravenous, intrapulmonary, subcutaneous or subepithelial route or by scarification. In the case of an accessible tumor, it is also possible to use direct injection into the site or in the vicinity of the tumor or a topical application. As vaccine, a composition according to the invention may be administered according to practices which are common in the field, for example as a single dose or as a dose repeated once or several times after a certain time interval. On the other hand, in the context of a curative treatment, it can be administered frequently for a period sufficient for the treatment to be effective. When the therapeutic agent is a viral vector, the virus is preferably in a live form. As regards a poxviral vector, it is preferable to use an attenuated strain such as the MVA strain or the thymidine kinase-negative Copenhagen strain. Finally, a recombinant viral vector may be attenuated by an appropriate chemical treatment known to persons skilled in the art. However, it is also possible to envisage injecting a killed recombinant vector.

According to a preferred embodiment, an antitumoral composition according to the invention comprises a therapeutically effective quantity of the therapeutic agent in combination with a pharmaceutically acceptable carrier. The carrier is chosen so as to allow its administration by injection into humans or into animals. It may also comprise a vehicle, a diluent and/or an adjuvant and may be provided in liquid or lyophilized form. In this regard, the combination of one or more substances capable of enhancing the transfection efficiency and/or the stability of the vector may be envisaged. These substances are widely documented in the literature which is accessible to persons skilled in the art (see for example Felgner et al., 1989, Proc. West. Pharmacol. Soc. 32, 115-121; Hodgson and Solaiman, 1996, Nature Biotechnology 14, 339-342, Remy et al., 1994, Bioconjugate chemistry 5, 647-654). By way of nonlimiting illustration, they may be polymers, lipids, in particular cationic lipids, liposomes, nuclear proteins and neutral lipids. A combination which may be envisaged is a plasmid vector combined with cationic lipids (DC-Chol, DOGS, and the like), and neutral lipids (DOPE). The composition may also be combined with other substances, in particular anticancer substances, it being possible for the latter to be administered separately or concomitantly. The ligand Flt3 is an example among others (Lynch et al., 1997, Nature Medicine 3, 625; Brasel et al., 1996, Blood 88, 2004-2012; Marakovsky et al., 1996, J. Exp. Med. 184, 1953-1962). It should be stated that the composition may be in the form of pseudoparticles when it comprises the polypeptides L1 and/or L2.

The subject of the present invention is also a recombinant vector comprising at least the sequences encoding an immunogenic polypeptide originating from an early and/or late region of a papillomavirus, said polypeptide having the characteristics defined above. It may in addition carry other sequences of interest, for example encoding one or more other immunogenic and/or immunostimulatory peptides, as described above.

The choice of a vector according to the invention is wide. It may be a plasmid or viral vector such as those cited above. A preferred embodiment consists of a poxviral vector and most particularly a vaccinia virus of the Copenhagen or MVA strain. The sites of insertion and the elements necessary for the expression of the sequences of interest to be expressed may be chosen from those mentioned above.

A preferred vector is a vaccinia virus of the Copenhagen or MVA strain into which there have been inserted:

(1) the sequences encoding an immunogenic polypeptide having a sequence homologous or identical to all or part of that shown in SEQ ID NO: 1,
(2) the sequences encoding an immunogenic polypeptide having a sequence homologous or identical to all or part of that shown in SEQ ID NO: 2,
(3) the sequences encoding an immunogenic polypeptide having a sequence homologous or identical to all or part of that shown in SEQ ID NO: 1 and an immunogenic polypeptide having a sequence homologous or identical to all or part of that shown in SEQ ID NO: 2,
(4) the sequences encoding an immunogenic polypeptide having a sequence homologous or identical to all or part of that shown in SEQ ID NO: 1, an immunogenic polypeptide derived from the protein L1 of a papillomavirus and/or an immunogenic polypeptide derived from the protein L2 of a papillomavirus,
(5) the sequences encoding an immunogenic polypeptide having a sequence homologous or identical to all or part of that shown in SEQ ID NO: 2, an immunogenic polypeptide derived from the protein L1 of a papillomavirus and/or an immunogenic polypeptide derived from the protein L2 of a papillomavirus, or
(6) the sequences encoding an immunogenic polypeptide having a sequence homologous or identical to all or part of that shown in SEQ ID NO: 1, an immunogenic polypeptide having a sequence homologous or identical to all or part of that shown in SEQ ID NO: 2, an immunogenic polypeptide derived from the protein L1 of a papillomavirus and/or an immunogenic polypeptide derived from the protein L2 of a papillomavirus.

It may optionally also include the sequences encoding IL2 or the polypeptide B7.1.

The present invention also relates to a viral particle prepared from a recombinant viral vector according to the invention. As regards an adenoviral vector, the viral particles may be generated by transfecting the vector into a complementation cell suitable for its deficiencies. Use may be made for example of the 293 line established from human embryonic kidney cells, which efficiently complements the E1 function (Graham et al., 1977, J. Gen. Virol. 36, 59-72), the A549-E1 line (Imler et al., 1996, Gene Therapy 3, 75-84) or a line allowing a double complementation (Yeh et al., 1996, J. Virol. 70, 559-565; Krougliak and Graham, 1995, Human Gene Therapy 6, 1575-1586; Wang et al., 1995 Gene Therapy 2, 775-783; international application WO97/04119). Complementation cell is understood to mean a cell capable of complementing in trans a defective vector in order to generate a viral particle. Said cell may not on its own complement all the defective functions of the vector and, in this case, it is possible to use a helper virus for a partial complementation. The viral particle may be recovered from the culture supernatant but also from the cells. One of the methods commonly used consists in lysing the cells by consecutive freeze/thaw cycles in order to recover the virions in the lysis supernatant. These may be amplified and purified according to prior art techniques (chromatographic method, ultracentrifugation in particular through a cesium chloride gradient and the like).

A retroviral particle can be obtained by transfecting the retroviral vector into an appropriate line, for example a line capable of providing in trans the viral polypeptides gag, pol and/or env whose sequences are deleted/nonfunctional in the vector. Such lines are described in the literature (PA317, Psi CRIP GP+Am-12 and the like).

As regards a poxviral vector, the general conditions for producing a vaccinia virus capable of expressing a heterologous gene are taught in European patent EP 83 286 and application EP 206 920. As for the MVA virus, it is more particularly described in Mayr et al. (1975, Infection 3, 6-14) and Sutter and Moss (1992, Proc. Natl. Acad. Sci. USA 89, 10847-10851). Briefly, the gene(s) to be transferred, placed under the control of appropriate elements for its (their) expression in vivo, is (are) inserted into a transfer vector including viral sequences on either side of the site of insertion. It is introduced into cells infected with an infectious vaccinia virus. The recombinant gene is integrated into the viral genome by homologous recombination between the homologous sequences of the infectious virus and of the transfer vector.

The recombinant vector or the viral particle may be optionally combined with one or more substances already mentioned, enhancing the transfection efficiency and/or the stability of the vector.

In the context of the present invention, said immunogenic polypeptide may be anchored in the protein structure surrounding the viral particle (capsid, envelope and the like).

Poxviruses are complex structures surrounded by multiple membranes. Two types of viral particles are produced: the intracellular mature virions (IMV) and the extracellular enveloped virions (EEV). The surface of the IMVs is composed of two superposed membranes and the envelope of the EEVs consists of four membranes including the plasma membrane. In accordance with the aims pursued by the present invention, the sequences encoding the immunogenic polypeptide may also be modified for insertion into one or other of the poxviral membranes (IMV or EEV) with the aim of enhancing the immune response. According to an advantageous embodiment, the immunogenic peptide is anchored in the outer membrane of the envelope of an EEV particle (Katz et al. 1997, AIDS Res. Hum. Retrov. 13, 1497-1500). To do this, the sequences encoding the C-terminal part of the B5R protein, a protein constituent of said outer membrane, are inserted in 3' of the coding region of the immunogenic polypeptide just upstream of the STOP codon. A completely preferred example is a fusion between the polypeptide E7 or one of its nononcogenic mutants and the 42 C-terminal residues of the B5R protein. The beneficial effect on the immune response may be evaluated by immuno-prophylactic and immunotherapeutic studies according to the protocol described in the following examples comparing the different formulations (native location, anchoring in the cell membrane, anchoring in the viral membrane).

The present invention also relates to the use of an antitumoral composition, of a recombinant vector or of a viral particle according to the invention, for the preparation of a medicament for the treatment or the prevention of cancer or of tumors and in particular of cancer of the cervix, of low-grade dysplasia of the cervix or of a papillomavirus infection. The preferred use is for the preparation of a medicament which can be injected by the intramuscular route.

Finally, the present invention also relates to a method for the treatment or prevention of the pathologies cited above, according to which a pharmaceutically effective quantity of an antitumoral composition, of a recombinant vector or of a viral particle according to the invention is administered to an individual requiring such a treatment.

BRIEF DESCRIPTION OF THE DRAWINGS

The present invention is illustrated with reference to the following figures.

EXAMPLES

Figure 1:
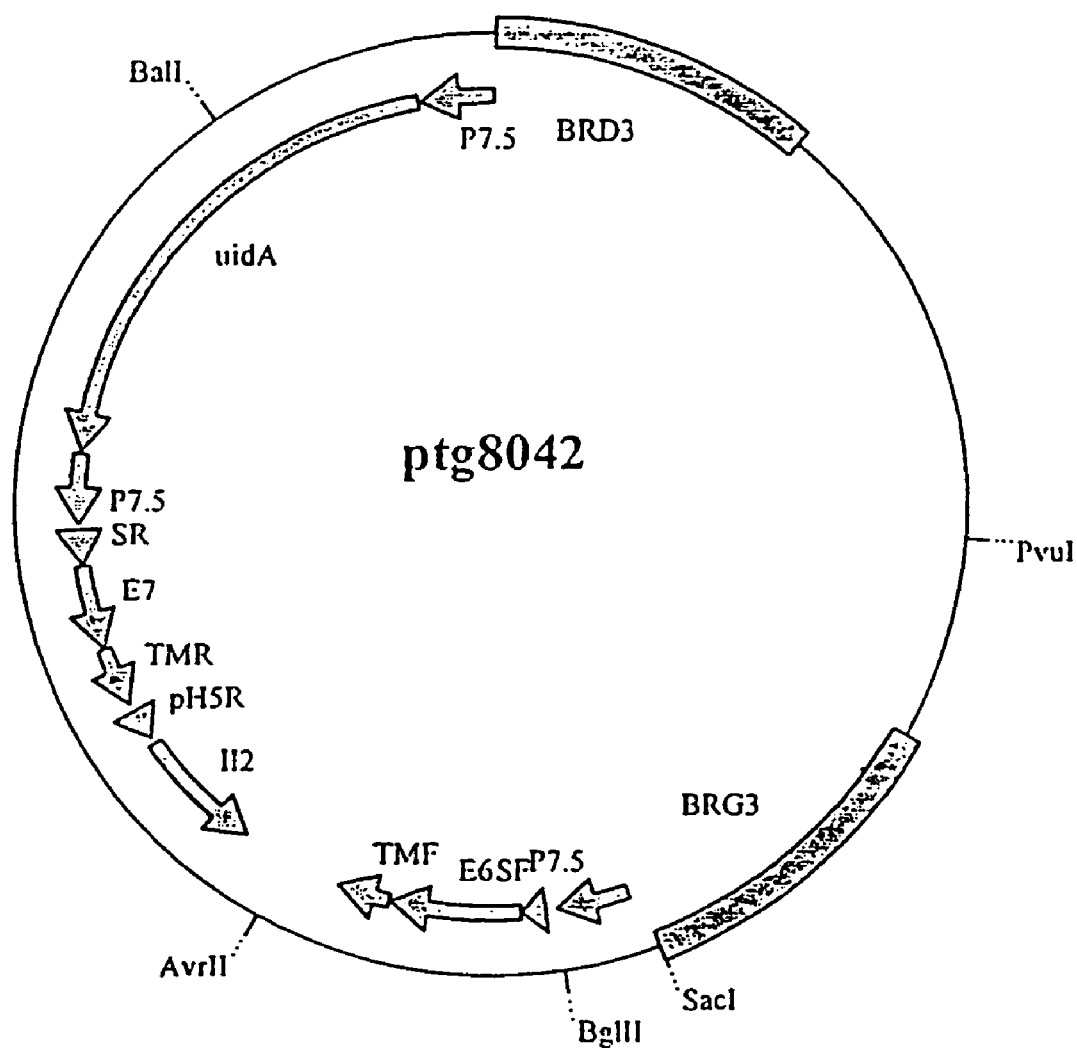
FIG. 1 is a schematic representation of pTG8042. BRG3 and BRD3 represent the left and right recombination arms allowing insertion at the level of the excision region III of the MVA virus. pTG8042 comprises a cassette for expressing the HPV16 E6 gene fused with the signal sequence (SF) and the transmembrane region (TMF) of the measles virus F protein, directed by the 7.5 k promoter; a cassette for expressing the IL-2 gene placed under the control of the promoter pH5R; a cassette for expressing the HPV16 E7 gene fused with the signal sequence (SR) and the transmembrane region (TMR) of the rabies glycoprotein, placed under the control of the p7.5 promoter and a cassette for expressing the gusA gene (uidA) placed under the control of the p7.5 promoter.

The present invention is more fully described, without being limited as a result, with the aid of the following examples.

The constructs described below are prepared according to general genetic engineering and molecular cloning techniques which are detailed in Maniatis et al., (1989, supra) or according to the manufacturer's recommendations when a commercial kit is used. Synthetic oligonucleotide-directed mutagenesis in vitro is carried out with the aid of the kit distributed by Amersham. The PCR amplification techniques are known to persons skilled in the art (see for example PCR Protocols—A guide to methods and applications, 1990, published by Innis, Gelfand, Sninsky and White, Academic Press Inc). As regards the repair of the restriction sites, the technique used consists of a filling of the protruding 5' ends with the aid of the large fragment of DNA polymerase I of E. coli (Klenow). As regards the cloning steps, the recombinant M13 bacteriophages are multiplied on the E. coli NM522 strain (Stratagene) in an agar minimum medium (agar 7.5%) or in a rich liquid LBM medium. The recombinant plasmids carrying the ampicillin-resistance gene are repeated in the E. coli strains C600 (Stratagene), BJ 5183 (Hanahan, 1983, J. Mol. Biol. 166, 557-580) and NM522 on agar or liquid medium supplemented with 100 μg/ml of antibiotic. The strain BJ5183 is preferably used when the cloning is carried out by homologous recombination (Bubeck et al., 1993, Nucleic Acid Res. 21, 3601-3602).

The construction of the recombinant vaccinia viruses is carried out according to the standard technology in the field which is disclosed in the documents already cited and in Mackett et al., (1982, Proc. Natl. Acad. Sci. USA 79, 7415-7419) and Mackett et al. (1984, J. Virol. 49, 857-864).

The tests in vivo (immunoprophylaxis or immunotherapy) are carried out on female C57B16 mice (C. Rivers Rouen, France) or nude mice (Janvier, Le Genest St. Isle, France) which were 6 to 8 weeks old. The animals are generally divided into groups of 20 (except when indicated) according to the viruses, the dose or the route of administration to be tested. The tumor cells TC1 (Wu, John Hopkins University, Baltimore, USA) are obtained from lung cells taken from C57B16 mice transduced with two retroviruses, one expressing the HPV-16 native E6 and E7 genes and the other expressing the ras oncogene. The cells are cultured in DMEM medium (Dubelcco Modified Eagles Medium) in the presence of G418 (0.5 mg/ml). The cells are used for the animal challenge after treatment with trypsin and 3 washes in isotonic medium.

Example 1

Construction of the Vectors Carrying the Sequences Encoding the Nononcogenic Mutants of HPV-16 E6 and E7 Provided with Transmembrane Localization Signals The E6 and E7 genes are isolated from the Caski cell line as described in examples 2 and 3 of European patent EP 0,462,187. Two constructs were derived from the clone M13E7/E6 containing the HPV-16 E6 and E7 genes so as to facilitate the subsequent cloning steps. The first, designated M13TG8188, results from the introduction, by directed mutagenesis, of PstI and BamHI sites respectively upstream and downstream of the E7 gene and the second, M13TG8189, comprises a PstI site upstream of the E6 gene. The introduction of point mutations upstream of an initiator ATG and downstream of a stop codon are within the capability of persons skilled in the art.

The combination of the HPV-16 E7 protein with the product of the retinoblastoma gene has been demonstrated by various authors (see for example Munger et al., 1989, EMBO J. 8, 4099-4105) and correlated with its transforming power. For obvious safety reasons, a nononcogenic mutant deleted for codons 21 to 26 of the native E7 protein which are involved in the transformation function is generated by directed mutagenesis of the vector M13TG8188 with the aid of the oligonucleotide oTG5118 (SEQ ID NO: 3). M13TG9104 carrying the mutated E7 gene, designated hereinafter E7*, is obtained.

The secretory and anchoring signals for the rabies glycoprotein are isolated from the rabies glycoprotein gene inserted in the form of a BglII fragment into pBR327 (pTG150 described in French patent 83 15716) and subcloned into a vector M13 (M13TG177). A BamHI site is introduced between these signals in phase with them by directed mutagenesis with the aid of the oligonucleotide oTG5745 (SEQ ID NO: 4). The resulting construct is called M13TG9128. The secretory and anchoring sequences are then isolated from M13TG9128 by PstI digestion and inserted in 3' of the natural promoter of the vaccinia virus p7.5 into the vector pTG5003 linearized with PstI, to give pTG5016. As a guide, pTG5003 is derived from pTG186poly (described in French patent 2,583,429) by SalI digestion, treatment with the Klenow fragment, and then digestion with SmaI and religation, so that it now contains in its polylinker only PstI and EcoRI sites excluding all others. The vector M13TG9104 is modified by directed mutagenesis with the aid of the oligonucleotides oTG6390 and oTG6880 (SEQ ID NO: 5 and 6) so as to bring into phase the E7* sequences and the secretory and anchoring signals for the rabies glycoprotein (designated in the text which follows E7*TMR). The resulting construct is called M13TG9150.

Likewise, it has been demonstrated that the HPV-16 E6 protein could interact with the product of expression of the tumor suppresser gene p53 (Crook et al., 1991, Cell 67, 547-556). The domain involved in this interaction has been clearly defined and is situated between residues 111 and 115 of the native protein. The vector M13TG9125 is generated by mutagenesis of M13TG8189 with the aid of the oligonucleotide oTG5377 (SEQ ID NO: 7). The E6 gene λ111-115 is designated hereinafter E6*.

The secretory and anchoring signals for the measles virus F protein are isolated by PCR from the plasmid construct pTG2148 (described in European patent EP 0,305,229) containing the DNA encoding the measles virus F protein. The fusion between these sequences and those encoding E6* is carried out by direct PCR: the secretory sequence is amplified with the aid of the oligonucleotides oTG10829 carrying in 5' an XbaI site (SEQ ID NO: 8) and oTG10830 covering the 5' end of E6 (SEQ ID NO: 9), the sequences encoding the mutant E6* are amplified from M13TG9125 with the aid of the oligonucleotides oTG10835 allowing the fusion with the 3' end of the secretory signal for the F protein (SEQ ID NO: 10) and oTG10836 allowing fusion with the 5' end of the anchoring sequence for the F protein (SEQ ID NO: 11). For the anchoring sequence, use is made of the primers oTG10833 allowing the fusion between the 3' of E6* and the 5' of the anchoring sequence (SEQ ID NO: 12) and oTG10834 creating in 3' the KpnI and SphI sites (SEQ ID NO: 13). The amplified fragment carrying the E6* sequences fused at the N- and C-terminals respectively with the membrane secretory and anchoring sequences of the F protein (designated in the text which follows E6*TMF is digested with XbaI and SphI and then inserted at the same sites into the vector M13TG131 (Kieny et al., 1983, Gene 26, 91-99). The construct thus obtained is called M13TG9199.

Example 2

Construction of the Recombinant Virus MVATG8042 Expressing the E6 and E7 Antigens of Transmembrane Location and Human IL-2

The MVA virus is derived from the Ankara strain of the vaccinia virus. It is not capable of generating infectious particles on mammalian cells but develops correctly on embryonic chicken fibroblasts. Its adaptation to these cells caused the excision of 6 regions which are nonessential for its development and its infectious cycle on this type of cells (disappearance of about 15% of the viral genome; Meyer et al., 1991, J. Gen. Virol. 72, 1031-1038). The integration of exogenous genetic material may be achieved at the level of any of these excision regions. In the context of the present invention, excisions II and III which are located at the level of the HindIII restriction fragments N and A respectively are used (Altenburger et al., 1989, Arch. Virol. 105, 15-27).

In a first instance, the vector pTG6019 allowing insertion into the region of excision III of the MVA virus is constructed. The homologous recombination arms on either side of the excision region III are isolated by PCR from the viral genome (see American patent U.S. Pat. No. 5,185,146) and the primers oTG7637 and oTG7638 (SEQ ID NO: 14 and 15) for the left arm and oTG7635 and oTG7636 (SEQ ID NO: 16 and 17) for the right arm. The amplified fragments are cloned at the EcoRI site of the vector pTG1E, to give pTG6019. The genetic material to be transferred is inserted between the two recombination arms. The vector pTG1E is similar to pTG1H (French patent 2,583,429) apart from the presence of an EcoRI adaptor in place of multiple cloning sites.

A cassette for expressing the marker gene gus A is inserted in the first place. The 7.5K promoter is first of all cloned into the BamHI site of pTG6019. pTG6021 is obtained into whose BamHI site is inserted the gus A gene generated in the form of a BglII-BamHI fragment. The latter may be obtained from the sequence disclosed in the literature. The resulting construct is called oTG6022. The presence of the marker will make it possible to distinguish the wild-type viruses from the recombinant viruses by detection of the enzymatic GUS activity with the XglcA substrate. A red color reveals the β-glucuronidase activity. However, with a view to a clinical application, it may be useful to be able to remove this bacterial marker from the final product after selecting the recombinant viruses. To do this, the capacity of vaccinia to delete the sequences between two homologous sites is exploited. Accordingly, a second p7.5K promoter is inserted downstream of the gus A gene in a sense orientation relative to that which directs the expression of the latter. The vector pTG6025 results from the insertion between the BamHI and SacI sites of pTG6022 of a p7.5K fragment provided with cohesive ends.

Moreover, the cDNA encoding human interleukin-2 is isolated from the plasmid pTG36 (French patent 2,583,770) by PstI digestion and inserted into the PstI site of the plasmid pTG186 (French patent 2,583,429), giving rise to a pTG188. The virus obtained by homologous recombination is called VVTG188. After BglII/EcoRI digestion, the IL-2 sequences are inserted in 3' of the natural vaccinia promoter pH5R at the BamHI/EcoRI sites of M13TG9132, to give M13TG9185. As a guide, the vector M13TG9132 is obtained from the insertion of the promoter of the H5R gene isolated by PCR from the viral genome into the phage M13TG6131, which is derived from M13TG131 (Kieny et al., 1983, supra) by mutation of the internal BglII site situated outside the multiple cloning sites.

The HPV-16 and IL-2 genes are then cloned into the region of excision III of the MVA genome. The E7*TMR sequences are isolated by BglII/HindIII digestion and inserted between the BamHI and HindIII sites of pTG6025 in 3' of the vaccinia promoter p7.5. The resulting construct is called pTG6050. A site for insertion of the cassette for expression of the human IL-2 gene by homologous recombination is created between the HindIII and KpnI sites of pTG6050 by insertion of the oligonucleotides oTG10502 and oTG10503 (SEQ ID NO: 18 and 19). The vector generated pTG6074 is then linearized by HindIII/KpnI digestion and the homologous recombination with the expression cassette pH5R-IL-2 isolated from M13TG9185 by BglII/EcoRI digestion is carried out. The resulting construct pTG6088 is finally linearized with KpnI and ligated with the E6*TMF gene isolated from M13TG9199 by KpnI/XbaI digestion and the promoter p7.5 isolated from M13TG9136 by XbaI/KpaI digestion. The resulting construct is called pTG8042 (FIG. 1). The vector M13TG9136 is obtained from M13TG5107 modified by directed mutagenesis with the aid of oTG5925 (creation of a PstI site in 3' of the p7.5 promoter; SEQ ID NO: 20) and oTG5924 (creation of a BamHI and KpnI site in 5' of the p7.5 promoter; SEQ ID NO: 21).

The virus MVATG8042 is generated by homologous recombination with the MVA genome according to the rules of the prior art. The isolation of the recombinants is facilitated by the presence of the gusA marker gene.

It is checked that the modification of the cell location of the HPV early antigens does not hamper their expression. Western blot analysis of cellular extracts infected with MVATG8042 with the aid of an anti-E7 antibody allows the detection of 3 bands having a molecular weight of between 20 and 35 kDa. This heterogeneity may be explained by the presence of a potential O-glycolysation site in the membrane anchoring region of the rabies glycoprotein. When the Western blot analysis is repeated in the presence of Phenyl-Gal-Nac (Phenyl N-acetyl-α-D-galactopyranoside, Sigma, P4023), only one form of 20 kDa is detected, which confirms the O-glycosylation of the product of expression of the E7*TMR gene.

The Western blot detection with the aid of an anti-E6 antibody of the product of expression of the E6*TMF gene reveals only one band migrating to the expected molecular weight of 20 kDa, which confirms the absence of post-translational modifications. As a guide, the abovementioned anti-E6 and E7 antibodies are rabbit antisera obtained by administering the purified antigen. However, any other specific antibody, whether monoclonal or polyclonal, may also be suitable.

The expression of the hIL-2 gene is evaluated by ELISA (Quantikine R&D Systems) and IL-2-dependent cell proliferation test. Depending on the culture conditions, the quantity of IL-2 produced varies from 200 to 800 ng/ml/24 h per $10^6$ cells infected with 0.1 pfu/cell.

Example 3

Efficiency in vivo of the Virus MVATG8042 (Immunotherapy)

C57BL6 mice are inoculated with $10^3$ BMK-16 myc cells implanted by the subcutaneous route. As a guide, the cell line is derived from kidney cells of newborn mice transfected with the HPV-16 genome and the murine c myc gene.

10⁷ pfu (plaque forming units) of MVATG8042 virus are then administered, also by the subcutaneous route on D3, D6 and D9 and the progression of the tumors monitored regularly. The treated mice exhibit a delay in tumor growth up to D15 compared with the controls consisting of animals which received a nonrecombinant MVA virus. Furthermore, the treatment is accompanied by a partial regression of the tumors at D30-35 which is not observed when an equivalent MVA is used which expresses the E6* and E7* mutants having a native nuclear location.

Example 4

Construction of the Recombinant Virus VVTG5095 Expressing the E7* Antigen of Transmembrane Location The E7*TMR sequences are isolated from M13TG9150 by BglII/BamHI digestion and inserted at the BamHI site of pTG5016. The resulting construct, called pTG5095, contains the E7* sequences fused with the secretory and anchoring signals for the rabies glycoprotein, under the control of the p7.5 promoter. The virus VVTG5095 is generated by homologous recombination with the vaccinia genome.

Example 5

Construction of the Recombinant Virus VVTG6002 Expressing the E7* Antigen of Transmembrane Location and the Immunostimulator B7.1

The human B7.1 gene is isolated from a Daudi human cell line by reverse PCR (RT-PCR) with the aid of the primers oTG6353 and oTG6352 (SEQ ID NO: 22 and 23) and inserted between the BglII and EcoRI sites of M13TG6131. M13TG9149 is obtained from which the BglII-EcoRI fragment is isolated which is subcloned between the same sites of M13TG5107, in 3' of the p7.5 promoter (M13TG5107 carries the p7.5 promoter sequences cloned into the BamHI site of M13TG130). The p7.5-B7.1 cassette is isolated from the construct thus obtained, called M13TG9152 by EcoRI/PstI digestion and introduced into the EcoRI site of pTG5095 with the aid of oTG1086 (5'AATTTGCA3'). The resulting construct is called pTG6002 and the recombinant viruses VVTG6002 are produced by homologous recombination with the vaccinia genome.

An equivalent construct is prepared by insertion of the cassettes for expressing the E7* and B7.1 genes into the excision region III of the MVAN33 genome according to the same technology as that developed in example 2.

Example 6

Efficiency in vivo of the Viruses VVTG5095 and VVTG6002 (Immuno-prophylaxis)

C57BL6 mice were vaccinated three times by the subcutaneous route with 10⁷ pfu of VVTG5095 or VVTG6002. Three days after the last immunization, these animals are challenged with 10³ E7W1 cells implanted subcutaneously. As a guide, the E7W1 cells are obtained from a murine lymphoma line transfected with a vector expressing the oncogenic E7 gene of HPV-16. The percentage survival of the animals as a function of time is compared with that obtained with control mice treated with 10⁷ pfu of a nonrecombinant vaccinia virus VVTG186 (derived from the vector TG186 described above). The monitoring of mortality shows a difference between the three groups. Whereas in the control group 100% of the animals died at D36, the survival of about a quarter of the animals vaccinated with VVTG5095 is observed. The protection is substantially enhanced with the construct VVTG6002 which includes the sequences encoding the B7.1 antigen.

Example 7

Construction of MVATG9936 Expressing the Modified Early Genes and the Late Genes of HPV16

The fragments encoding the HPV16 L1 and L2 proteins are isolated by PCR from genomic DNA of Caski cells (ATCC 1550) according to general prior art techniques. The amplification fragment carrying the L1 sequences is subcloned into M13TG130 (Kieny et al., 1983, Gene 26, 91-99), to give the construct M13TG8171. The sequence of the cloned L1 gene reveals several mutations compared with the sequence contained in Genebank (accession K02718): C in place of an A at position 248, C in place of an A at position 253, G in place of an A at position 537, G in place of a C in position 682, G in place of an A at position 874, insertion of a triplet ACT at position 1393, deletion of a triplet GAT at position 1390. The sequence is corrected by point mutagenesis so as to bring it into conformity with that published by Zhou et al. (1991, Virology 185, 251-257) and to introduce silent mutations at the level of the TTTTTNT sequences which constitute potential sites for early transcription termination which are capable of interfering with the early phase of development of vaccinia. The technique of site-directed mutagenesis is within the capability of persons skilled in the art. The vector carrying the corrected sequence is designated M13TG4041.

The insertion of the PCR fragment carrying the L2 sequences into the vector M13TG6131 leads to M13TG9126. 5 point mutations are identified compared with the sequence disclosed in Genebank: C in place of a T at position 378, A in place of a G at position 691, A in place of a G at position 702, G in place of an A at position 990 and C in place of an A at position 1092. As a guide, the vector M13TG6131 is derived from M13TG131 (Kieny et al., 1983, Gene 26, 91-99) by mutation of the internal BglII site situated outside of the multiple cloning sites.

The vector M13TG4041 is digested with XbaI-SacI and the fragment carrying the L1 sequences is inserted between the XbaI-SacI sites of M13TG9126 downstream of the L2 gene and in the opposite direction. The construct thus generated is called M13TG4042. The L1 and L2 sequences are then isolated by BglII digestion and subcloned between the BglII and BamHI sites of the vector M13TG4052 containing the synthetic promoter p11K7.5, which results from the fusion of the late p11K and early p7.5 promoters. Of the two orientations, the one which places the L1 gene downstream of the promoter, which is designated M13TG4055, is selected. The expression cassette carrying the pH5R promoter and the hIL-2 gene is then isolated from pTG8042 by HindIII digestion before being introduced into the HindIII site of M13TG4055 situated between the L1 and L2 genes. Finally, the construct obtained, M13TG4057, is digested with BglII and the fragment carrying the HPV16 late sequences is inserted into the BamHI site of M13TG4060, which results from the cloning of the synthetic promoter p4BK1L. The latter is a hybrid promoter between the early promoter p4B (Davidson and Moss, 1989, J. Mol. Biol. 210, 749-769) and the late promoter pK1L (Davidson and Moss, 1989, J. Mol. Biol. 210, 771-784). M13TG4062 is obtained which comprises the L1 gene under the control of p11K7.5, the cassette pH5R-IL2 and the L2 gene under the control of p4BK1L in the opposite orientation relative to the L1 sequences.

A polycistronic cassette is constructed which contains the sequences encoding E7*TMR and E6*TMF. In the first instance, the IRES sequences of the EMC virus (encephalomyocarditis; Genbank accession M22458) are isolated by conventional techniques in the form of an EcoRI-NcoI fragment introduced downstream of the E7*TMR gene between the EcoRI and NcoI sites of pTG6002 (example 5), to give pTG8084. The E6*TMF gene is then amplified by PCR with the aid of appropriate primers, creating an NcoI site at each 5' end. The BglII-NcoI fragment carrying the E7*TMR gene and the IRES sequences which is obtained from pTG8084 and the PCR fragment carrying the E6*TMF gene digested by NcoI and SacI are reassembled in the vector M13TG6131 (example 2) previously digested with BglII and SacI. M13TG4059 is obtained. The unit E7*TMR-IRES-E6*TMF is then isolated from the latter in the form of a BglII fragment and inserted into the BamHI site of pTG8093 downstream of the p7.5K promoter (pTG8093 results from the cloning of the p7.5K promoter into the vector pTG6025. The construct thus obtained is designated pTG9901.

Figure 2:
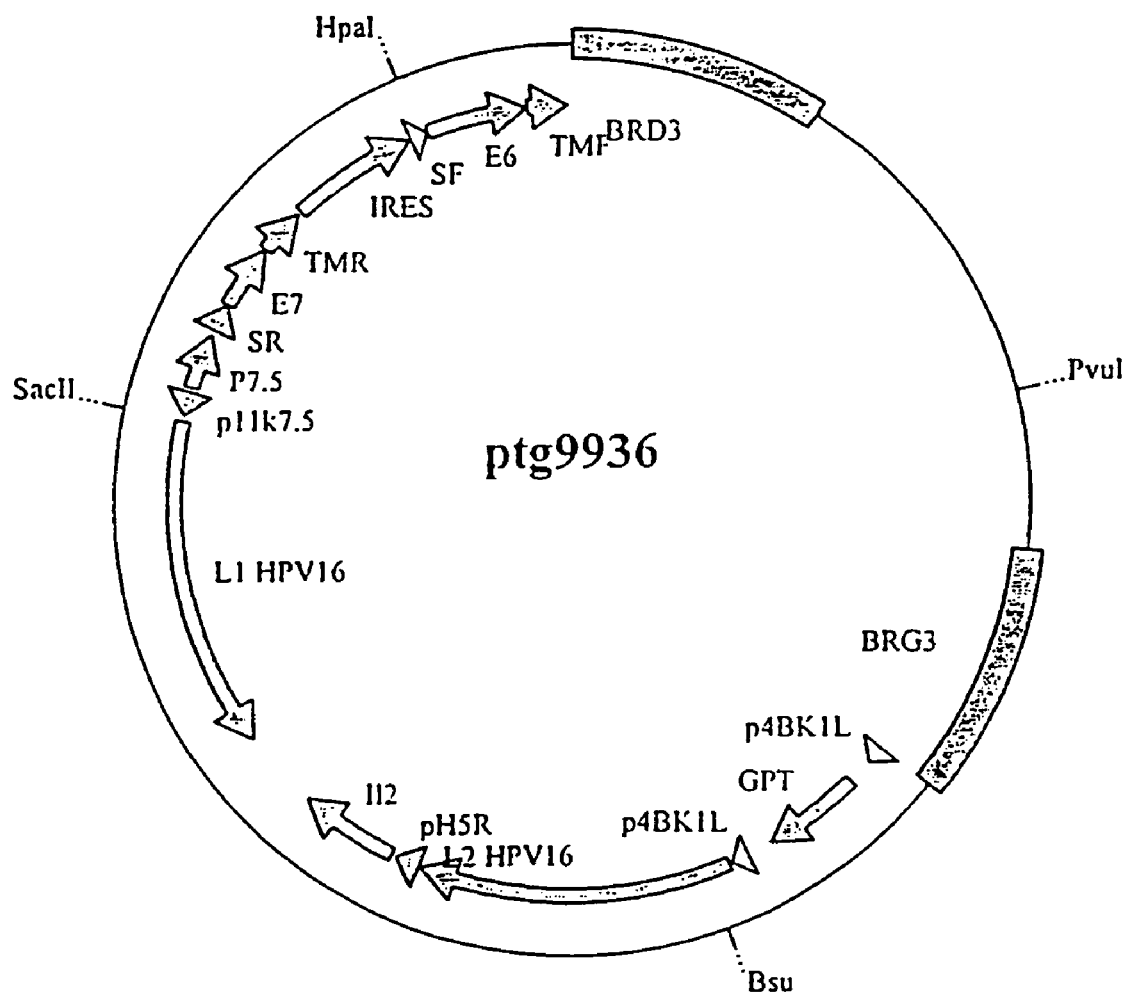
FIG. 2 is a schematic representation of the vector pTG9936. BRG3 and BRD3 represent the left and right recombination arms allowing insertion at the level of the excision region III of the MVA genome. The pTG9936 carries the promoter p4BK1L directing the expression of the gpt marker gene, the promoter p4BK1L directing the expression of the HPV16 L2 gene, the promoter pH5R directing the expression of IL-2, the promoter p11k7.5 directing the expression of the HPV16 L1 gene, the promoter p7.5 directing the expression of the HPV16 E7 gene fused with the signal sequence (SR) and the transmembrane region (TMR) of the rabies virus glycoprotein followed by an IRES sequence and the HPV16 E6 gene fused with the signal sequence (SF) and the transmembrane region (TMF) of the measles virus F protein.

The SacI fragment of M13TG4062 is cloned into the SacI site of pTG9901, to give pTG9902. The selectable gpt gene (Falkner and Moss, 1988, J. Virol. 62, 1849-1854) is assembled with the late and IL2 genes in the vector p poly II (Lathe et al., 1987, Gene 57, 193-201) in the following manner. The first is isolated from M13TG4076 (this vector contains the gpt gene flanked at its two ends by p4BK1L promoter sequences) by BglII-NcoI digestion and the second from pTG9902 by NcoI-SacI digestion. The purified fragments are cloned between the BglII-SacI sites of p poly II. pTG9933 is obtained from which the SacI fragment is obtained which is introduced into the vector pTG9901 cleaved by SacI. The construct thus obtained, pTG9936, is illustrated in FIG. 2.

The MVATG9936 viruses are generated by homologous recombination with the MVAN33 genome. The isolation of clones may be carried out according to the prior art rules.

Example 8

Efficiency of the Viruses in Immunoprophylaxis

A. Importance of the Formulation of the Viruses (Experiment N121)

The aim of this preclinical study is to compare the viral strain (Copenhagen vaccinia virus against MVA) and the formulation (transmembrane presentation against native nuclear location) in terms of antitumoral protection.

C57B16 mice are vaccinated three times with $10^7$ pfu of virus. The injections are made every ten days (D1, D11 and D21) by the intraperitoneal route. The animals are challenged 7 days after the last immunization by subcutaneous administration into their right-hand side of $5 \times 10^4$ TC1 cells. Eight groups of 20 animals are formed according to the virus and the solution administered, respectively:

1 MVATG8042 (example 2, E6*TMF, E7*TMR, IL-2),
2 MVATG6037 (example 5, E7*TMR, B7.1),
3 VVTG5095 (example 4, E7*TMR),
4 MVATG6090 (E6*, E7*, IL-2),
5 VVTG5061x188 (E6*, E7*, IL-2),
6 VVTG186 (nonrecombinant vaccinia virus),
7 MVAN33 (nonrecombinant MVA virus), and
8 a saline solution (PBS).

Groups 1 to 3 are vaccinated with the viruses of the present invention expressing at least one transmembrane HPV antigen whereas groups 4 and 5 received viruses expressing HPV16 early antigens of native nuclear location and groups 6 to 8 nonrecombinant control viruses or a saline solution. It should be stated that the viruses MVATG6090 and VVTG5061x188 are described in international application WO98/04705. The percentage survival of the animals of the different groups is monitored for the 12 weeks which follow the tumoral challenge. The results may be summarized in the following manner.

In general, the mortality is high in the three control groups, reaching 95% (with the viruses MVAN33 and VV186) and 81% (with PBS).

A significant increase in the survival of the animals immunized with the viruses expressing the HPV nuclear antigens is observed. Thus, 55% of the mice which received the virus MVATG6090 are free of tumors whereas the administration of VVTG5061x188 induces a tumor rejection level of 75%.

On the other hand, the great majority of the animals vaccinated with the viruses expressing the HPV16 transmembrane antigens rejected their tumor or exhibit a substantial delay in tumor growth. More precisely, 100% rejection is observed with MVATG8042, 95% with MVATG6037 and 90% with VVTG5095.

Figure 3:
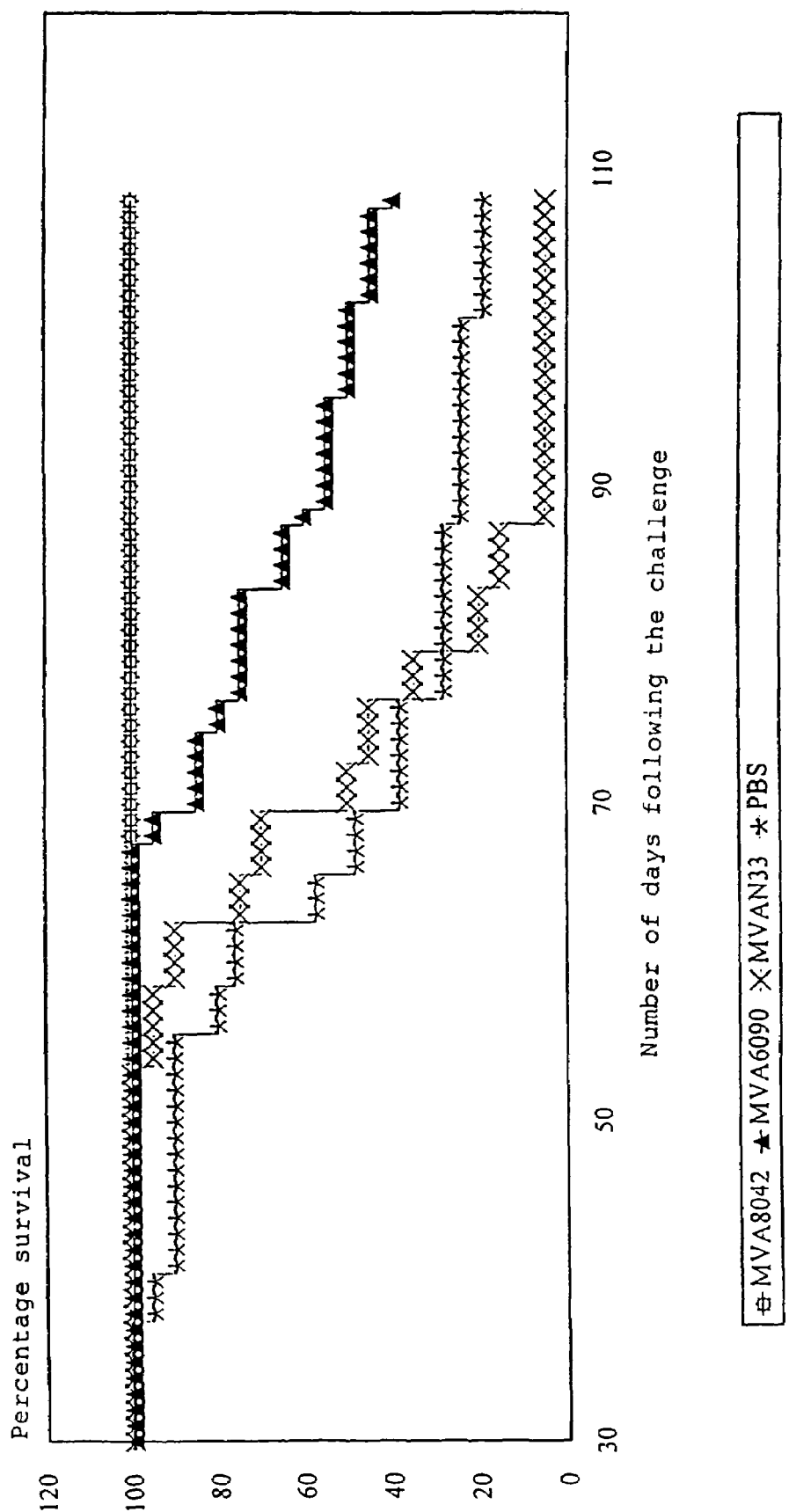
FIG. 3 illustrates experiment N121 by presenting the percentage survival as a function of time (in days) of the animals vaccinated before tumoral challenge with the virus MVATG8042, MVATG6090, MVAN33 or with PBS.

FIG. 3 presents the survival curves obtained with the animals vaccinated with MVATG8042 and MVATG6090 compared with the controls (MVAN33 and PBS).

As a whole, these data demonstrate the absence of a significant difference between the viruses derived from a Copenhagen vaccinia virus and from an MVA and the better immunogenic conferred by the membrane presentation. Of all the viruses tested, the virus MVATG8042 is the most effective since it gives rise to 100% tumor rejection in this animal model of immunoprophylaxis.

B. Study of the Memory Response (Experiment N122)

The C57B16 mice are immunized by the intraperitoneal route with $10^7$ pfu of virus at D1, D11 and D21 before being challenged at D82 by subcutaneous administration into their right-hand side of $5 \times 10^4$ TC1 cells. Eight groups identical to the previous experiment (N121) are formed. The progression of the tumors is monitored as a function of time. The data obtained 50 days after the tumoral challenge confirm that the most effective virus in terms of tumor rejection is the virus MVATG8042. Its administration protects 100% of the animals, indicating its capacity to induce a long-term immunity.

C. Dose Effect (Experiment N127)

Figure 4:
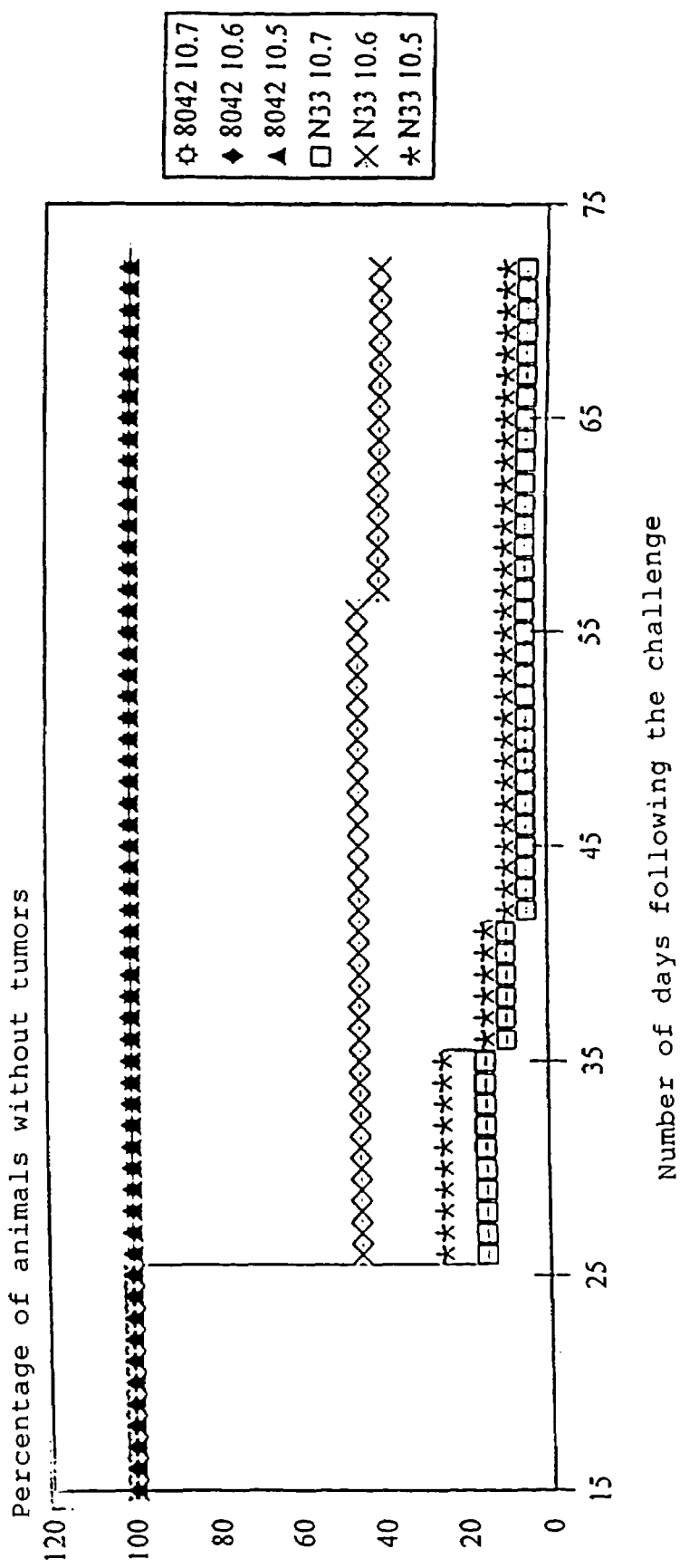
FIG. 4 represents the percentage of animals without tumors as a function of time (in days) after administration of $10^7$, $10^6$ and $10^5$ pfu of virus MVAN33 or MVATG8042 (experiment N127).

C57B16 mice are immunized by the intraperitoneal route at D1, D11 and D21 with $10^5$, $10^6$, or $10^7$ pfu of MVATG8042 virus before being challenged at D28 by subcutaneous administration into their right-hand side of $5 \times 10^4$ TC1 cells. The control animals receive identical quantities of MVAN33. The progression of the tumors is monitored twice a week for 12 weeks. The results (FIG. 4) show 100% protection regardless of the dose of MVATG8042 administered whereas the great majority of the control animals develop tumors. These data confirm the efficacy of the MVATG8042 virus even at low dose.

D. Effect of the Route of Administration (Experiment N134)

Figure 5:
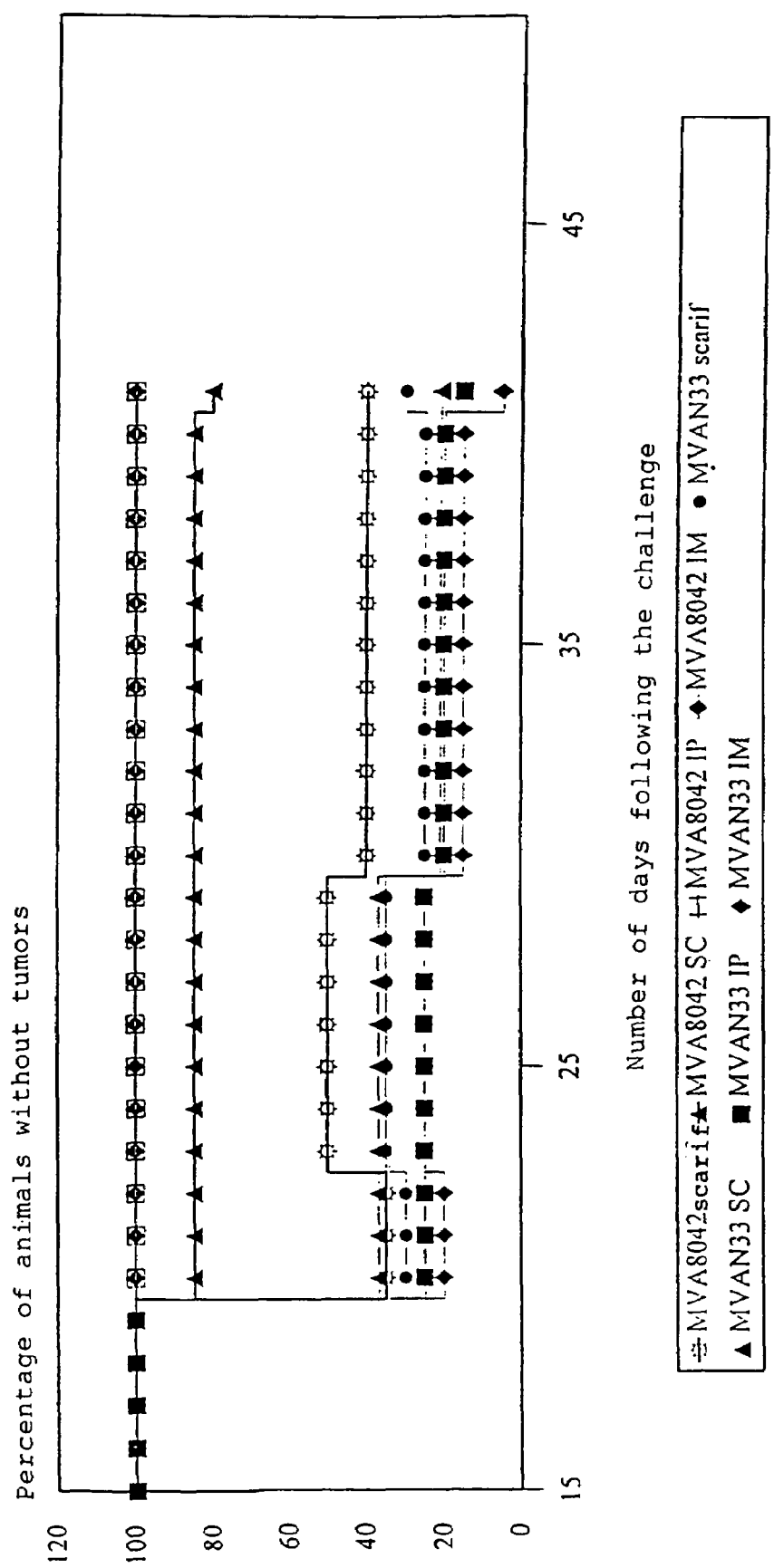
FIG. 5 illustrates experiment N134 by presenting the percentage survival as a function of time (in days) of the animals treated with the virus MVATG8042 or with the control MVAN33 by scarification, subcutaneously (SC), intraperitoneally (IP) or intramuscularly (IM).

The C57B16 mice are immunized by various routes of administration (scarification, subcutaneously, intraperitoneally or intramuscularly) at D1, D11 and D21 with $10^7$ pfu of virus before being challenged at D44 by subcutaneous administration into their right-hand side of $5\times10^4$ TC1 cells. The progression of the tumors is monitored twice a week for 12 weeks. As shown in FIG. 5, the intraperitoneal or intramuscular routes give the highest levels of protection with the virus MVATG8042.

Example 9

Efficacy of the Viruses in Immunotherapy

A. Efficacy of the Viruses in an Immunotherapy Context (Experiment N125)

The aim of this study is to compare the therapeutic capacities, towards a preestablished tumor, of the viruses exhibiting the HPV antigens in a membrane or nuclear form. To do this, $5\times10^4$ TC1 cells are administered by the subcutaneous route into the right-hand side of C57B16 mice (D0). $10^7$ pfu of virus are then injected by the intraperitoneal route at D7, D14 and D21. Four groups of animals are formed according to the virus administered: respectively MVAN33 (negative control), a saline solution of tris-HCl/NaCl (negative control), MVATG8042 (transmembrane formulation) and MVATG6090 (nuclear formulation). The progression of the tumors is evaluated twice a week for 12 weeks. The results show a better efficacy of the membrane presentation in terms of antitumoral protection in a therapeutic context. 100% of the mice which received MVATG8042 survived 140 days after implantation of the tumor cells whereas the percentage is about 60% for the animals injected with MVATG6090 and much lower for the control animals.

B. Toxicity Studies—Effect of the Dose

It is important to verify the absence of virulence of the viruses before envisaging their application to human tumors. $10^6$ or $10^7$ pfu of MVATG8042 or MVAN33 virus or a wild-type Copenhagen vaccinia virus (VVwt) are administered to nude mice (5 animals/group) by the intracranial route. The survival of the mice is monitored for 20 days. and the resulted presented in the following table 1

TABLE 1

| virus | Number of surviving nude mice | |
|---|---|---|
| | $10^6$ pfu | $10^7$ pfu |
| MVAN33 | 5/5 | 5/5 |
| MVATG8042 | 5/5 | 5/5 |
| VVwt | — | 0/5 |

No side effect is detected following the intracranial administration of $10^7$ pfu of the MVATG8042 virus whereas all the mice treated with the wild-type vaccinia virus died three days after the injection. The control MVA virus is not toxic for the animals either, which confirms its attenuation compared with the vaccinia virus already described in the literature.

The invention claimed is:

1. An antitumoral composition for the treatment of an HPV related cancerous or precancerous condition, wherein the composition comprises at least one recombinant vector or a viral particle comprising said recombinant vector, wherein said recombinant vector comprises a sequence encoding at least one immunogenic polypeptide of a papillomavirus, wherein said immunogenic polypeptide is modified by linking to a membrane anchoring sequence so as to have a membrane location at the surface of the cells in which it is expressed.

2. The antitumoral composition according to claim 1, wherein the immunogenic polypeptide is further modified by linking to a secretory sequence.

3. The antitumoral composition according to claim 1, wherein said membrane anchoring sequence is selected from the group consisting of a membrane anchoring sequence of rabies glycoprotein, HIV virus env glycoprotein, and measles virus F protein.

4. The antitumoral composition according to claim 1, wherein said immunogenic polypeptide originates from an early and/or late region of the papillomavirus.

5. The antitumoral composition according to claim 4, wherein said immunogenic polypeptide is derived from a polypeptide of the early region of the papillomavirus.

6. The antitumoral composition according to claim 4, wherein said immunogenic polypeptide is derived from the L1 or L2 polypeptide of the papillomavirus.

7. The antitumoral composition according to claim 1, wherein at least one immunogenic polypeptide is derived from an early polypeptide and at least one immunogenic polypeptide is derived from a late polypeptide of the papillomavirus.

8. The antitumoral composition according to claim 1, wherein at least one immunogenic polypeptide is such that:

(1) said immunogenic polypeptide has a sequence having a degree of identity greater than 90% to that shown in SEQ ID NO: 1, (2) said immunogenic polypeptide has a sequence having a degree of identity greater than 90% to that shown in SEQ ID NO: 2, (3) said immunogenic polypeptide has a sequence having a degree of identity greater than 90% to that shown in SEQ ID NO: 1 and an immunogenic polypeptide having a sequence having a degree of identity greater than 90% to that shown in SEQ ID NO: 2, (4) said immunogenic polypeptide has a sequence having a degree of identity greater than 90% to that shown in SEQ ID NO: 1, an immunogenic polypeptide derived from the L1 protein of a papillomavirus and/or an immunogenic polypeptide derived from the L2 protein of a papillomavirus, (5) said immunogenic polypeptide has a sequence having a degree of identity greater than 90% to that shown in SEQ ID NO: 2, an immunogenic polypeptide derived from the L1 protein of a papillomavirus and/or an immunogenic polypeptide derived from the L2 protein of a papillomavirus, or (6) said immunogenic polypeptide has a sequence having a degree of identity greater than 90% to that shown in SEQ ID NO: 1, an immunogenic polypeptide having a sequence having a degree of identity greater than 90% to that shown in SEQ ID NO: 2, an immunogenic polypeptide derived from the L1 protein of a papillomavirus and/or an immunogenic polypeptide derived from the L2 protein of a papillomavirus.

9. The antitumoral composition according to claim 1, wherein said recombinant vector comprises, in addition, the sequences encoding at least one compound which enhances the antitumoral effect of said composition.

10. The antitumoral composition according to claim 9, wherein said compound enhancing the antitumoral effect is an immunostimulator.

11. The antitumoral composition according to claim 10, wherein said immunostimulator is selected from the group consisting of interleukin-2, interleukin-7, and interleukin-12.

12. The antitumoral composition according to claim 1, containing a pharmaceutically acceptable carrier allowing its administration by injection into humans or into animals.

13. The antitumoral composition according to claim 1, wherein said membrane anchoring sequence is inserted at the C-terminal end of said immunogenic polypeptide.

14. The antitumoral composition according to claim 2, wherein said secretory sequence is selected from the group consisting of secretory sequences of rabies glycoprotein, HIV virus env glycoprotein and measles virus F protein.

15. The antitumoral composition according to claim 2, wherein said secretory sequence is inserted at the N-terminal end of said immunogenic polypeptide.

16. The antitumoral composition according to claim 5, wherein said polypeptide of the early region of a papillomavirus is E6 or E7.

17. The antitumoral composition according to claim 1, wherein said papillomavirus is selected from the group consisting of HPV-16, HPV-18, HPV-31, HPV-33 and HPV-45.

18. The antitumoral composition according to claim 12, C wherein said administration is by intramuscular, and/or subcutaneous route.

* * * * *

SEQUENCE LISTING

```
<160> NUMBER OF SEQ ID NOS: 23

<210> SEQ ID NO 1
<211> LENGTH: 243
<212> TYPE: PRT
<213> ORGANISM: Artificial Sequence
<220> FEATURE:
<223> OTHER INFORMATION: Description of Artificial Sequence:Derived
      from human papillomavirus, strain HPV-16, E6 protein fused F
      protein signals, clone E6*TMF.

<400> SEQUENCE: 1

Met Gly Leu Lys Val Asn Val Ser Ala Ile Phe Met Ala Val Leu Leu
  1               5                  10                  15

Thr Leu Gln Thr Pro Thr Gly Gln Ile His Trp Gly Met His Gln Lys
             20                  25                  30

Arg Thr Ala Met Phe Gln Asp Pro Gln Glu Arg Pro Arg Lys Leu Pro
         35                  40                  45

Gln Leu Cys Thr Glu Leu Gln Thr Thr Ile His Asp Ile Ile Leu Glu
     50                  55                  60

Cys Val Tyr Cys Lys Gln Gln Leu Leu Arg Arg Glu Val Tyr Asp Phe
 65                  70                  75                  80

Ala Phe Arg Asp Leu Cys Ile Val Tyr Arg Asp Gly Asn Pro Tyr Ala
                 85                  90                  95

Val Cys Asp Lys Cys Leu Lys Phe Tyr Ser Lys Ile Ser Glu Tyr Arg
            100                 105                 110

His Tyr Cys Tyr Ser Leu Tyr Gly Thr Thr Leu Glu Gln Gln Tyr Asn
        115                 120                 125
```

```
Lys Pro Leu Cys Asp Leu Leu Ile Arg Cys Ile Asn Cys Gln Lys Pro
    130                 135                 140
Leu Gln Arg His Leu Asp Lys Lys Gln Arg Phe His Asn Ile Arg Gly
145                 150                 155                 160
Arg Trp Thr Gly Arg Cys Met Ser Cys Cys Arg Ser Ser Arg Thr Arg
                165                 170                 175
Arg Glu Thr Gln Leu Gly Leu Ser Ser Thr Ser Ile Val Tyr Ile Leu
            180                 185                 190
Ile Ala Val Cys Leu Gly Gly Leu Ile Gly Ile Pro Ala Leu Ile Cys
            195                 200                 205
Cys Cys Arg Gly Arg Cys Asn Lys Lys Gly Glu Gln Val Gly Met Ser
    210                 215                 220
Arg Pro Gly Leu Lys Pro Asp Leu Thr Gly Thr Ser Lys Ser Tyr Val
225                 230                 235                 240
Arg Ser Leu

<210> SEQ ID NO 2
<211> LENGTH: 185
<212> TYPE: PRT
<213> ORGANISM: Artificial Sequence
<220> FEATURE:
<223> OTHER INFORMATION: Derived from human papillomavirus, strain
      HPV-16, E7 fusion signals of the rabies glycoprotein, clone
      E7*TMR.

<400> SEQUENCE: 2

Met Val Pro Gln Ala Leu Leu Phe Val Pro Leu Leu Val Phe Pro Leu
  1               5                  10                  15
Cys Phe Gly Lys Phe Pro Ile Gly Ser Met His Gly Asp Thr Pro Thr
                 20                  25                  30
Leu His Glu Tyr Met Leu Asp Leu Gln Pro Glu Thr Thr Gln Leu Asn
             35                  40                  45
Asp Ser Ser Glu Glu Glu Asp Glu Ile Asp Gly Pro Ala Gly Gln Ala
         50                  55                  60
Glu Pro Asp Arg Ala His Tyr Asn Ile Val Thr Phe Cys Cys Lys Cys
 65                  70                  75                  80
Asp Ser Thr Leu Arg Leu Cys Val Gln Ser Thr His Val Asp Ile Arg
                 85                  90                  95
Thr Leu Glu Asp Leu Leu Met Gly Thr Leu Gly Ile Val Cys Pro Ile
            100                 105                 110
Cys Ser Gln Lys Pro Arg Ser Tyr Val Leu Leu Ser Ala Gly Ala Leu
            115                 120                 125
Thr Ala Leu Met Leu Ile Ile Phe Leu Met Thr Cys Cys Arg Arg Val
        130                 135                 140
Asn Arg Ser Glu Pro Thr Gln His Asn Leu Arg Gly Thr Gly Arg Glu
145                 150                 155                 160
Val Ser Val Thr Pro Gln Ser Gly Lys Ile Ile Ser Ser Trp Glu Ser
                165                 170                 175
His Lys Ser Gly Gly Glu Thr Arg Leu
            180                 185

<210> SEQ ID NO 3
<211> LENGTH: 36
<212> TYPE: DNA
<213> ORGANISM: Artificial Sequence
<220> FEATURE:
<223> OTHER INFORMATION: Derived from human papillomavirus, strain
```

HPV-16, synthetic oligonucleotide oTG5118 (E7 deleted 21 26),
anti-sense.

<400> SEQUENCE: 3
tctgagctgt catttaattg agttgtctct ggttgc                              36

<210> SEQ ID NO 4
<211> LENGTH: 42
<212> TYPE: DNA
<213> ORGANISM: Artificial Sequence
<220> FEATURE:
<223> OTHER INFORMATION: Derived from rabies virus, mutagenesis
      oligonucleotide oTG5745, non anti-sense

<400> SEQUENCE: 4
tgcactcagt aatacatagg atccaatagg gaatttccca aa                       42

<210> SEQ ID NO 5
<211> LENGTH: 38
<212> TYPE: DNA
<213> ORGANISM: Artificial Sequence
<220> FEATURE:
<223> OTHER INFORMATION: Synthetic oligonucleotide oTG6390, anti-sense.

<400> SEQUENCE: 5
gtatctccat gcatggatcc tgcagggttt ctctacgt                            38

<210> SEQ ID NO 6
<211> LENGTH: 36
<212> TYPE: DNA
<213> ORGANISM: Artificial Sequence
<220> FEATURE:
<223> OTHER INFORMATION: Synthetic oligonucleotide oTG6880, anti-sense.

<400> SEQUENCE: 6
ggatccgcca tggtagatct tggtttctga gaacag                              36

<210> SEQ ID NO 7
<211> LENGTH: 32
<212> TYPE: DNA
<213> ORGANISM: Artificial Sequence
<220> FEATURE:
<223> OTHER INFORMATION: Derivative from rabies virus, strain HPV-16,
      synthetic oligonucleotide oTG5377 (E6 deleted 111 to 115),
      anti-sense.

<400> SEQUENCE: 7
tgtccagatg tctttgcagt ggcttttgac ag                                  32

<210> SEQ ID NO 8
<211> LENGTH: 34
<212> TYPE: DNA
<213> ORGANISM: Artificial Sequence
<220> FEATURE:
<223> OTHER INFORMATION: Synthetic oligonucleotide oT10829, non
      anti-sense.

<400> SEQUENCE: 8
gcgcgctcta gaattatggg tctcaaggtg aacg                                34

<210> SEQ ID NO 9
<211> LENGTH: 35
<212> TYPE: DNA
<213> ORGANISM: Artificial Sequence
<220> FEATURE:
<223> OTHER INFORMATION: Synthetic oligonucleotide oTG10830, anti-sense.

```
<400> SEQUENCE: 9
cagttctctt tggtgcatg ccccaatgga tttga                              35

<210> SEQ ID NO 10
<211> LENGTH: 38
<212> TYPE: DNA
<213> ORGANISM: Artificial Sequence
<220> FEATURE:
<223> OTHER INFORMATION: Synthetic oligonucleotide oTG10835, non
      anti-sense.

<400> SEQUENCE: 10
atgctagtgc tcgataaacc cagctgggtt tctctacg                          38

<210> SEQ ID NO 11
<211> LENGTH: 35
<212> TYPE: DNA
<213> ORGANISM: Artificial Sequence
<220> FEATURE:
<223> OTHER INFORMATION: Synthetic oligonucleotide oTG10836, anti-sense.

<400> SEQUENCE: 11
tcaaatccat tggggcatgc accaaaagag aactg                             35

<210> SEQ ID NO 12
<211> LENGTH: 38
<212> TYPE: DNA
<213> ORGANISM: Artificial Sequence
<220> FEATURE:
<223> OTHER INFORMATION: Synthetic oligonucleotide oTG10833, non
      anti-sense.

<400> SEQUENCE: 12
cgtagagaaa cccagctggg tttatcgagc actagcat                          38

<210> SEQ ID NO 13
<211> LENGTH: 36
<212> TYPE: DNA
<213> ORGANISM: Artificial Sequence
<220> FEATURE:
<223> OTHER INFORMATION: Synthetic oligonucleotide oTG10834, anti-sense.

<400> SEQUENCE: 13
gcgggcatgc ggtacctcag agcgaccta catagg                             36

<210> SEQ ID NO 14
<211> LENGTH: 32
<212> TYPE: DNA
<213> ORGANISM: Artificial Sequence
<220> FEATURE:
<223> OTHER INFORMATION: Derivated from vaccinia virus, strain modified
      Ankara, synthetic oligonucleotide oTG7637 (PCR III region), non
      anti-sense.

<400> SEQUENCE: 14
gggggggaat tcagtaaact tgactaaatc tt                                32

<210> SEQ ID NO 15
<211> LENGTH: 39
<212> TYPE: DNA
<213> ORGANISM: Artificial Sequence
<220> FEATURE:
<223> OTHER INFORMATION: Derivated from vaccinia virus, strain modified
      Ankara, synthetic oligonucleotide oTG7638 (PCR III region),
      anti-sense.

<400> SEQUENCE: 15
```

```
ggggggggat ccgagctcac cagccaccga aagagcaat                    39
```

<210> SEQ ID NO 16
<211> LENGTH: 32
<212> TYPE: DNA
<213> ORGANISM: Artificial Sequence
<220> FEATURE:
<223> OTHER INFORMATION: Derived from vaccinia virus, strain modified
      Ankara, synthetic oligonucleotide oTG7635 (PCR III region), non
      anti-sense.

<400> SEQUENCE: 16

```
ggggggggat ccggaaagtt ttataggtag tt                           32
```

<210> SEQ ID NO 17
<211> LENGTH: 30
<212> TYPE: DNA
<213> ORGANISM: Artificial Sequence
<220> FEATURE:
<223> OTHER INFORMATION: Derived from vaccinia virus, strain modified
      Ankara, synthetic oligonucleotide oTG7636 (PCR III region),
      anti-sense.

<400> SEQUENCE: 17

```
ggggggaat tctttgtatt tacgtgaacg                               30
```

<210> SEQ ID NO 18
<211> LENGTH: 77
<212> TYPE: DNA
<213> ORGANISM: Artificial Sequence
<220> FEATURE:
<223> OTHER INFORMATION: Synthetic oligonucleotide oTG10502, non
      anti-sense.

<400> SEQUENCE: 18

```
agcttttat tctatactta aaaatgaaa ataaactcga gttgtcaaag catcatctca  60
acactgactt gaggtac                                            77
```

<210> SEQ ID NO 19
<211> LENGTH: 69
<212> TYPE: DNA
<213> ORGANISM: Artificial Sequence
<220> FEATURE:
<223> OTHER INFORMATION: Synthetic oligonucleotide oTG10503, anti-sense.

<400> SEQUENCE: 19

```
ctcaagtcag tgttgagatg atgctttgac aactcgagtt tatttcatt ttttaagtat  60 agaataaaa                                                     69
```

<210> SEQ ID NO 20
<211> LENGTH: 39
<212> TYPE: DNA
<213> ORGANISM: Artificial Sequence
<220> FEATURE:
<223> OTHER INFORMATION: Synthetic oligonucleotide oTG5925, anti-sense.

<400> SEQUENCE: 20

```
tcagatctgt cgagggatct gcagcttctt ctagaggta                    39
```

<210> SEQ ID NO 21
<211> LENGTH: 44
<212> TYPE: DNA
<213> ORGANISM: Artificial Sequence
<220> FEATURE:
<223> OTHER INFORMATION: Synthetic oligonucleotide oTG5924, non -continued

```
anti-sense.

<400> SEQUENCE: 21
agtgaattgc tgcaggtacc cggatccgca tcgactatcg acat          44

<210> SEQ ID NO 22
<211> LENGTH: 35
<212> TYPE: DNA
<213> ORGANISM: Artificial Sequence
<220> FEATURE:
<223> OTHER INFORMATION: Derivated from Homo sapiens, strain Daudi cell
      line, PCR primer oTG6353 (cloning B7.1), non anti-sense.

<400> SEQUENCE: 22
tcagcccctg aattctgcgg acactgttat acagg                    35

<210> SEQ ID NO 23
<211> LENGTH: 33
<212> TYPE: DNA
<213> ORGANISM: Artificial Sequence
<220> FEATURE:
<223> OTHER INFORMATION: Derivated from Homo sapiens, strain Daudi cell
      line, PCR primer oTG6352 (cloning B7.1), anti-sense.

<400> SEQUENCE: 23
ttgaccctaa agatctgaag ccatgggcca cac                      33
```